United States Patent [19]

Tovey et al.

[11] Patent Number: 5,674,230

[45] Date of Patent: Oct. 7, 1997

[54] SURGICAL SUTURING APPARATUS WITH LOCKING MECHANISMS

[75] Inventors: H. Jonathan Tovey, Milford; Corbett W. Stone, Newtown, both of Conn.; Stephen W. Zlock, Hawthorne, N.Y.; David A. Nicholas, Trumbull; Paul A. Scirica, Huntington, both of Conn.; Philip Richardson, Maes-y-coed, Meidrim, St. Clears, Dyfed SA 33 5QA, Wales; Margaret Pamela Richardson, Dyfed, both of United Kingdom

[73] Assignees: United States Surgical Corporation, Norwalk, Conn.; Philip Richardson; Margaret P. Richardson, both of Wales, United Kingdom

[21] Appl. No.: 527,125

[22] Filed: Sep. 12, 1995

Related U.S. Application Data

[63] Continuation of Ser. No. 319,841, Oct. 7, 1994, abandoned, which is a continuation-in-part of Ser. No. 134,145, Oct. 8, 1993, abandoned.

[51] Int. Cl.$^6$ ............................................. A61B 17/10
[52] U.S. Cl. ................................. 606/139; 606/143
[58] Field of Search ...................... 606/139 J, 142–148

[56] References Cited

U.S. PATENT DOCUMENTS

| | | |
|---|---|---|
| 1,037,864 | 9/1912 | Carlson et al. |
| 1,131,163 | 3/1915 | Saunders et al. |
| 1,293,565 | 2/1919 | Smit. |
| 1,449,087 | 3/1923 | Bugbee. |
| 1,876,792 | 9/1932 | Thompson. |
| 2,213,830 | 9/1940 | Anastasi. |
| 2,880,728 | 4/1959 | Rights. |
| 3,090,038 | 5/1963 | Curtis. |
| 3,349,772 | 10/1967 | Rygg. |
| 3,470,875 | 10/1969 | Johnson. |
| 3,807,407 | 4/1974 | Schweizer. |

(List continued on next page.)

FOREIGN PATENT DOCUMENTS

| | | |
|---|---|---|
| 0482881 | 4/1992 | European Pat. Off. |
| 337579 | 4/1904 | France. |
| 9109097 | 9/1991 | Germany. |
| 4124383 | 5/1992 | Germany. |
| 4124381 | 8/1992 | Germany. |
| 4127812 | 2/1993 | Germany. |
| 4139628 | 3/1993 | Germany. |

(List continued on next page.)

OTHER PUBLICATIONS

Aesculap Catalog, p. 401 (Date: 1905).

*Primary Examiner*—Michael Buiz
*Assistant Examiner*—Kevin Truong

[57] ABSTRACT

An apparatus for manipulating a surgical needle is disclosed, comprising a body portion, a first needle receiving jaw mounted for movement on a distal end of the body portion and having a first needle engaging member, a second needle receiving jaw mounted for movement on the distal end of the body portion and having a second needle engaging member, the second needle engaging member being operatively interconnected to the first needle engaging member for relative reciprocal movement therewith, wherein each of the first and second needle receiving jaws has a recess for receipt of a portion of a surgical needle therein. The first and second needle engaging members are mounted for alternate reciprocal movement into and out of locking engagement with the surgical needle. The apparatus also includes a wheel rotatably mounted within the body portion with a proximal end portion of each of the first and second needle engaging members connected to opposing sides of the wheel such that rotation of the wheel simultaneously retracts one of the needle engaging members and advances the other. Also disclosed is a method of manipulating a surgical needle inside a body cavity using a surgical instrument having a control mechanism, a first jaw and a second jaw, where at least one of the jaws is mounted for movement between a first position adjacent the other jaw and a second position spaced apart from the other jaw.

18 Claims, 27 Drawing Sheets

U.S. PATENT DOCUMENTS

| | | |
|---|---|---|
| 3,842,840 | 10/1974 | Schweizer . |
| 3,901,244 | 8/1975 | Schweizer . |
| 3,946,740 | 3/1976 | Bassett . |
| 4,021,896 | 5/1977 | Stierlein . |
| 4,109,658 | 8/1978 | Hughes . |
| 4,161,951 | 7/1979 | Scanlon, Jr. . |
| 4,164,225 | 8/1979 | Johnson et al. . |
| 4,236,470 | 12/1980 | Stenson . |
| 4,345,601 | 8/1982 | Fukuda . |
| 4,373,530 | 2/1983 | Kilejian . |
| 4,471,781 | 9/1984 | Di Giovanni et al. . |
| 4,491,135 | 1/1985 | Klein . |
| 4,580,567 | 4/1986 | Schweitzer et al. . |
| 4,621,640 | 11/1986 | Mulhollan et al. . |
| 4,635,638 | 1/1987 | Weintraub et al. . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 5,059,201 | 10/1991 | Asnis . |
| 5,100,421 | 3/1992 | Christoudias . |
| 5,171,257 | 12/1992 | Ferzli . |
| 5,181,919 | 1/1993 | Bergman et al. . |
| 5,207,693 | 5/1993 | Phillips . |
| 5,217,471 | 6/1993 | Burkhart . |
| 5,242,458 | 9/1993 | Bendel et al. . |
| 5,254,126 | 10/1993 | Filipi et al. . |
| 5,261,917 | 11/1993 | Hasson et al. . |
| 5,281,220 | 1/1994 | Blake, III . |
| 5,336,230 | 8/1994 | Leichtling et al. . |
| 5,454,823 | 10/1995 | Richardson et al. ............ 606/148 |

FOREIGN PATENT DOCUMENTS

| | | |
|---|---|---|
| 1505514 | 9/1984 | U.S.S.R. . |
| 1103854 | 8/1994 | U.S.S.R. . |
| 1249853 | 10/1971 | United Kingdom . |
| 2260704 | 9/1991 | United Kingdom . |
| 9301750 | 2/1993 | WIPO . |

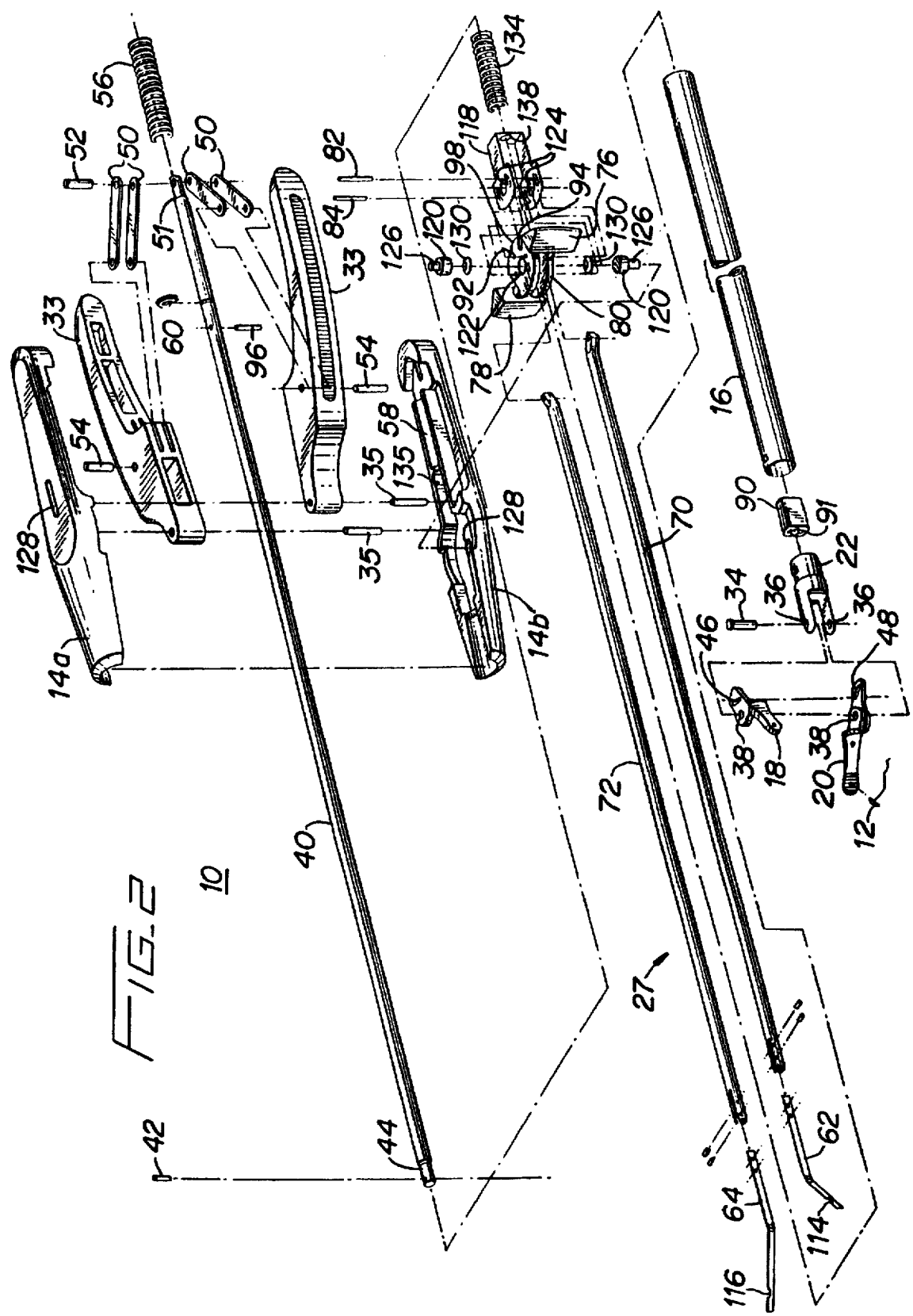

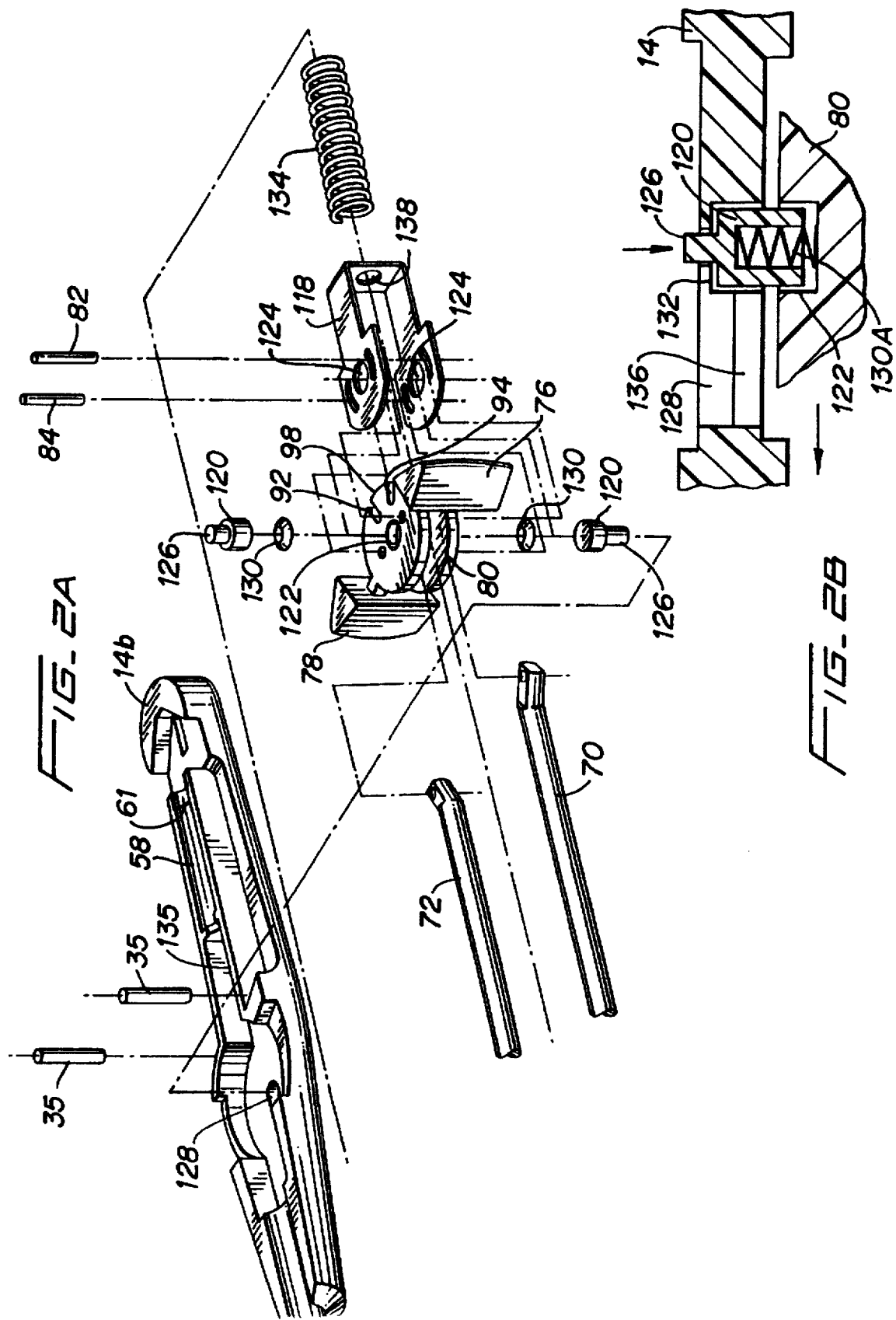

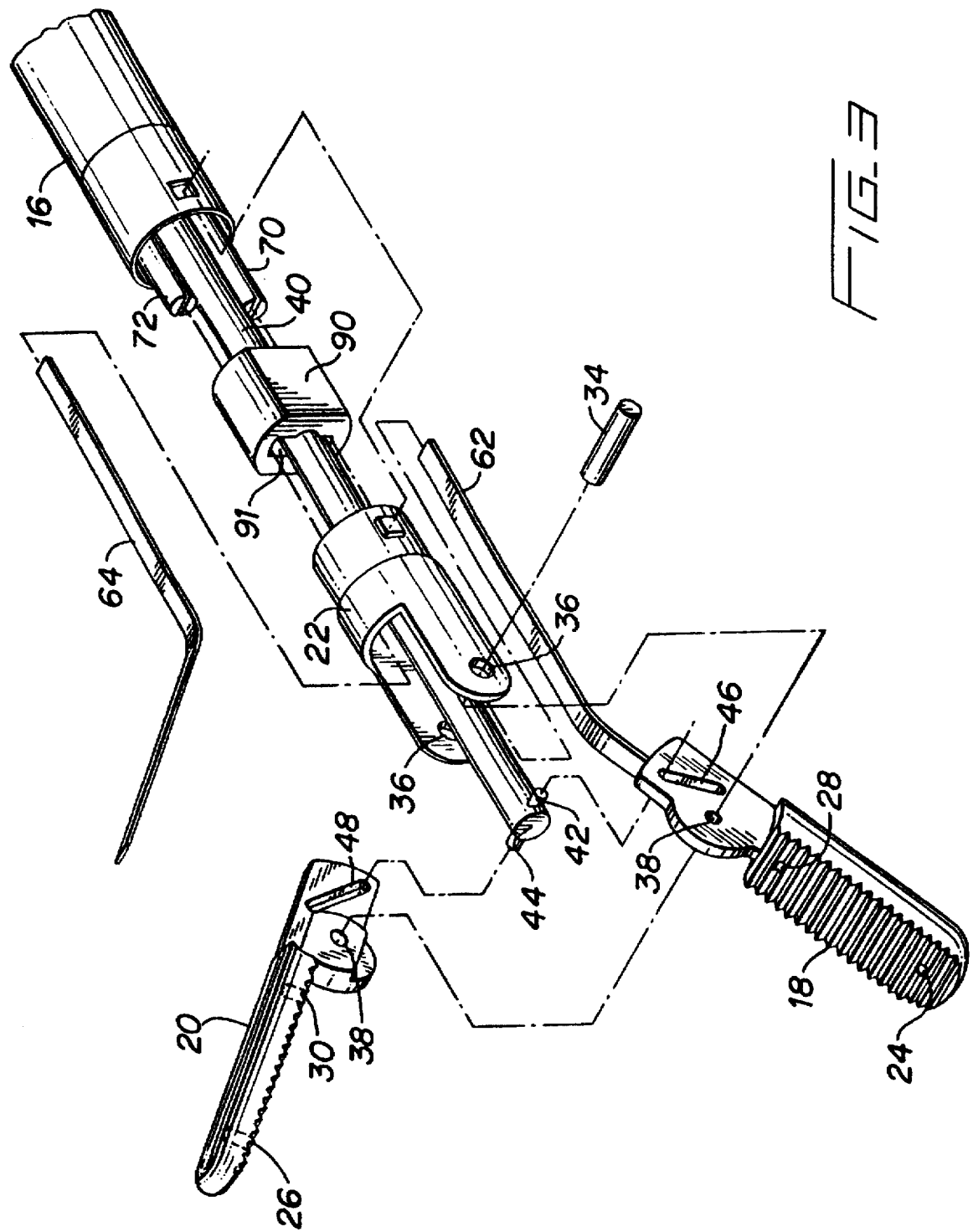

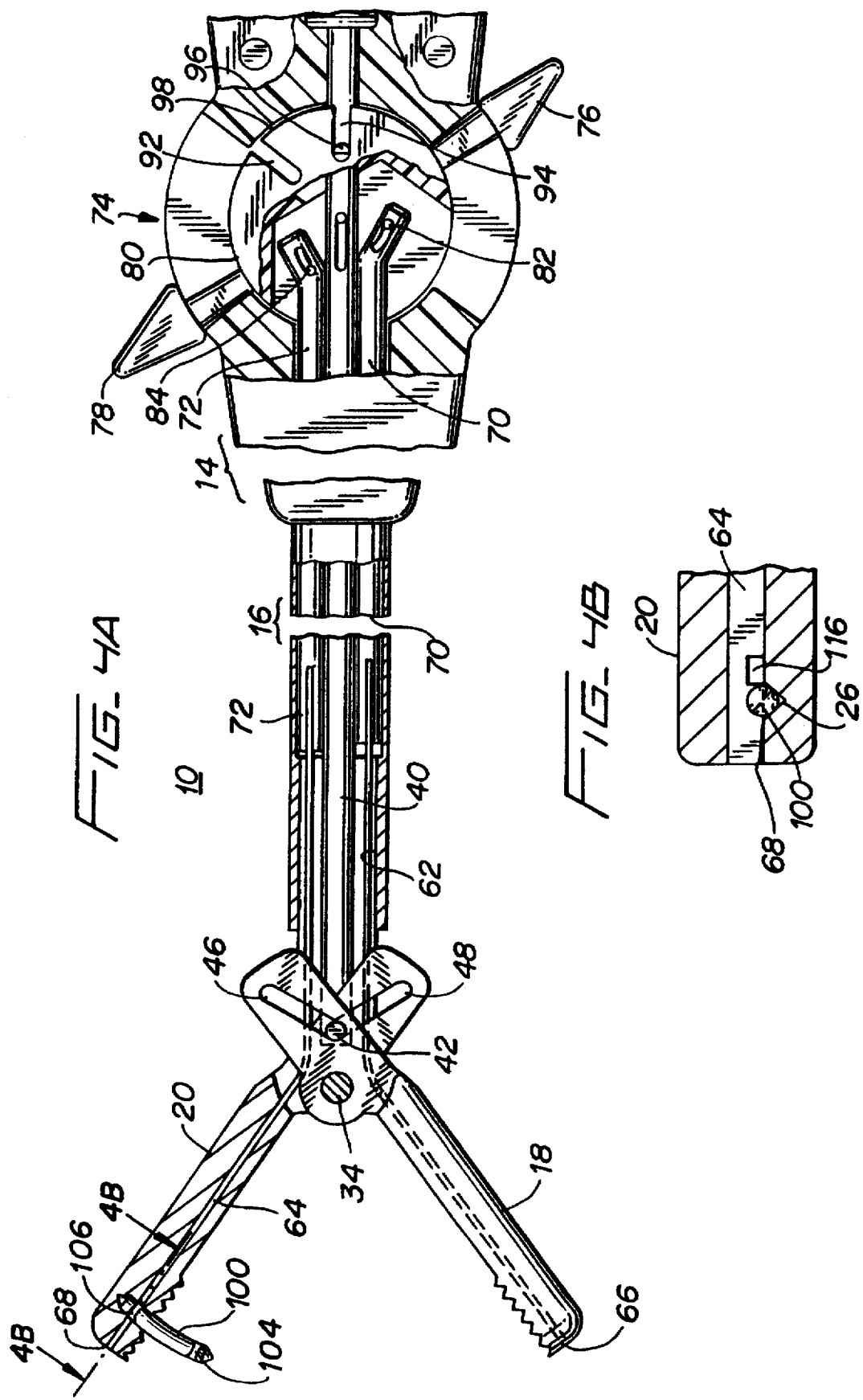

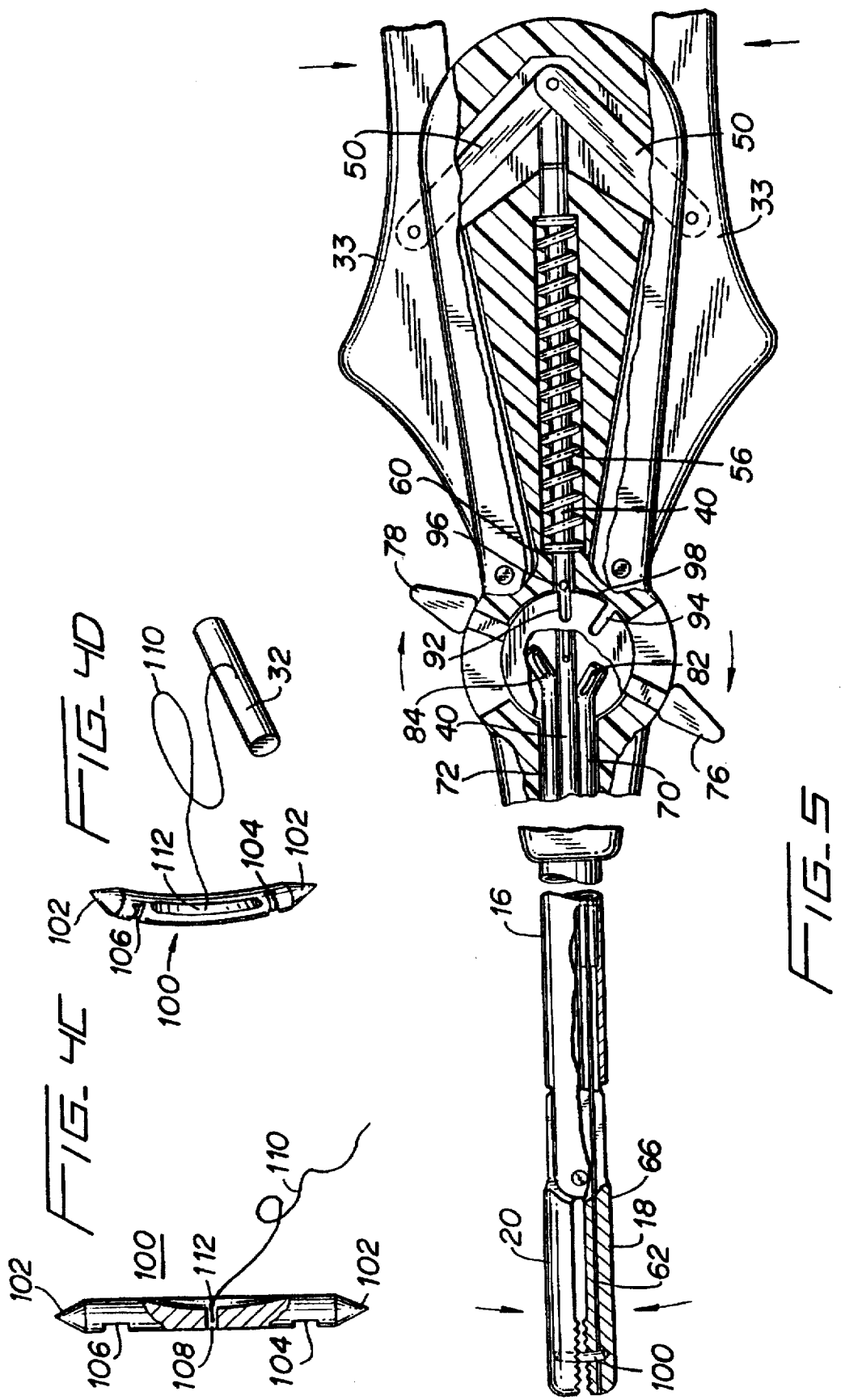

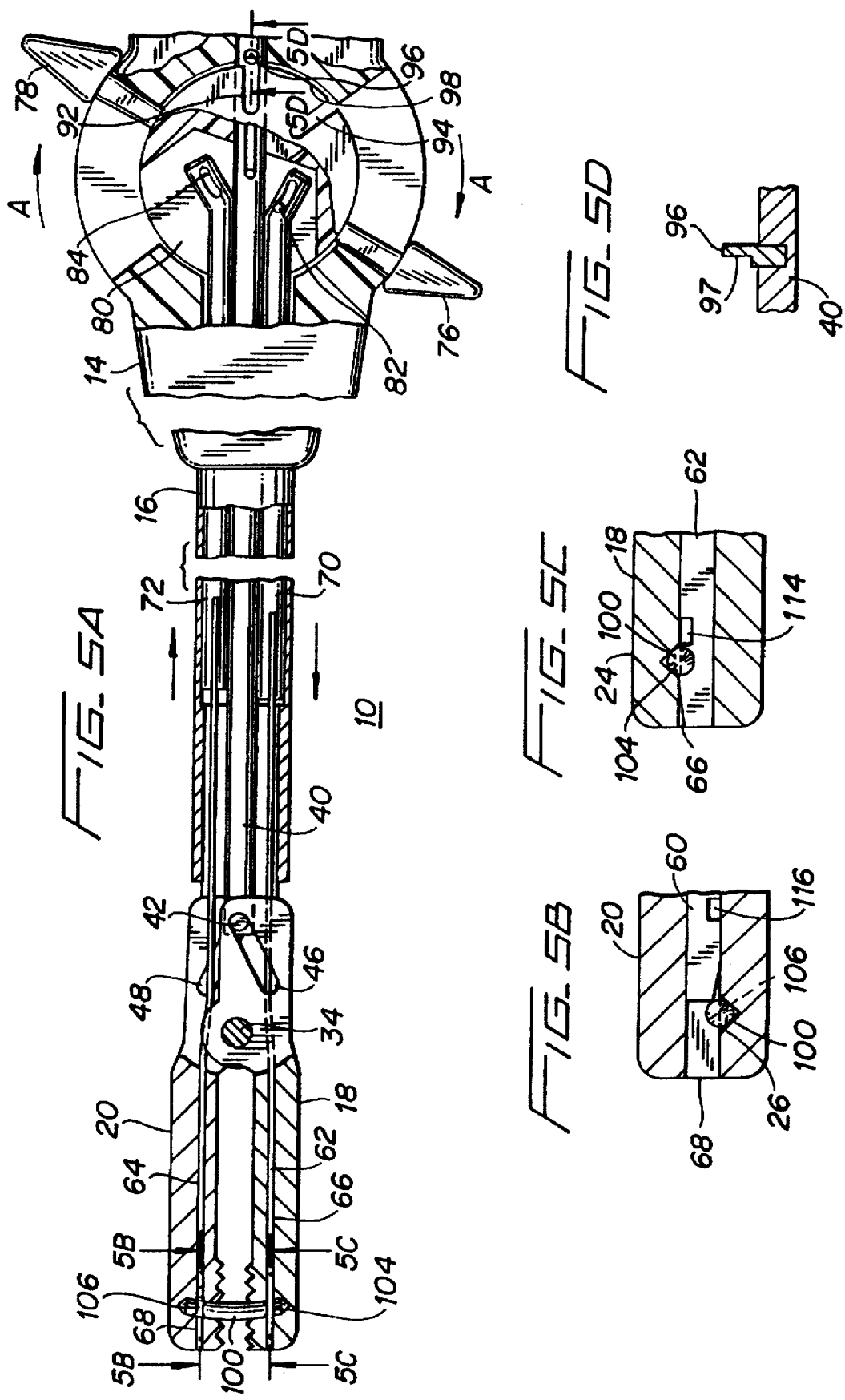

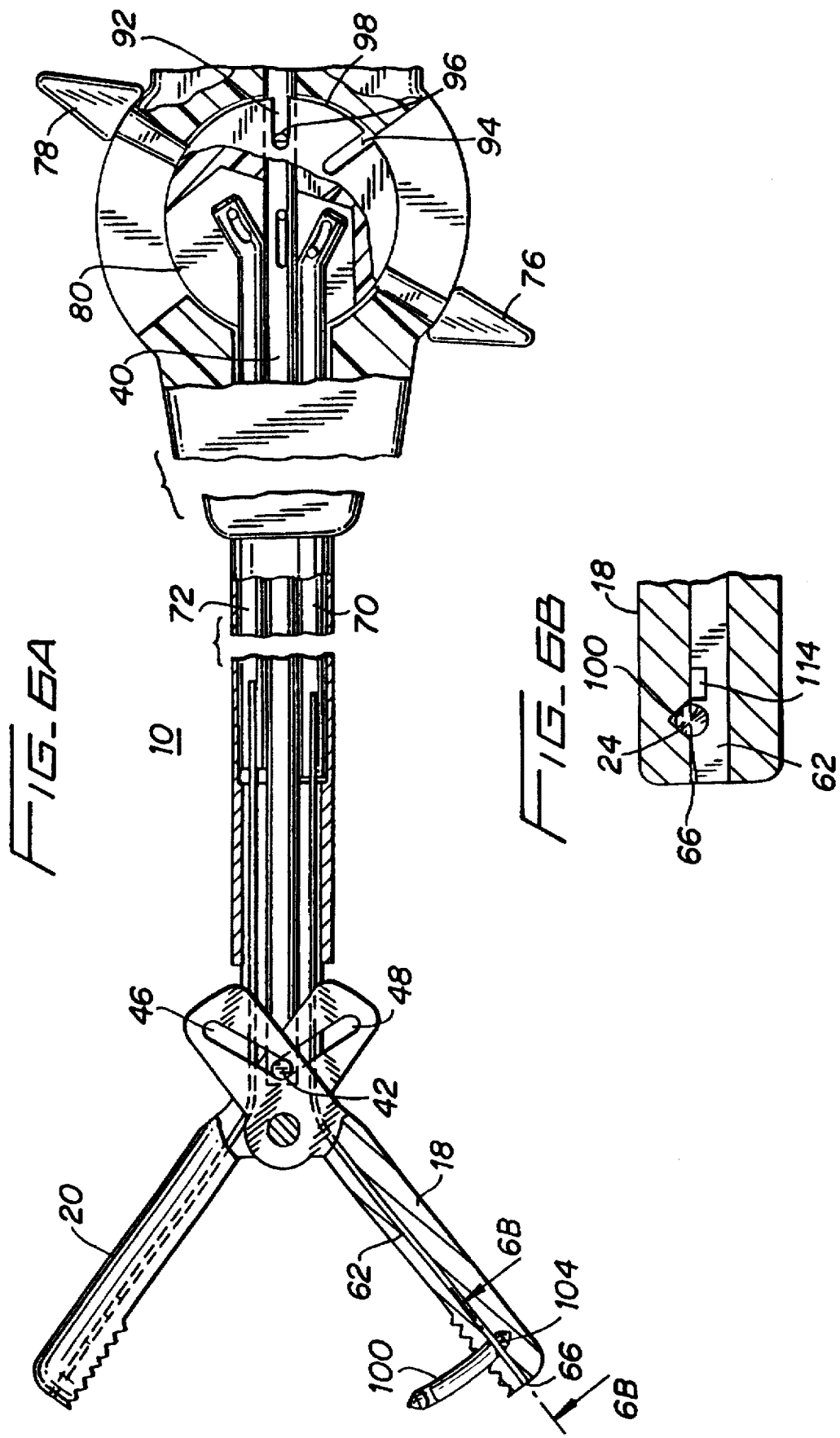

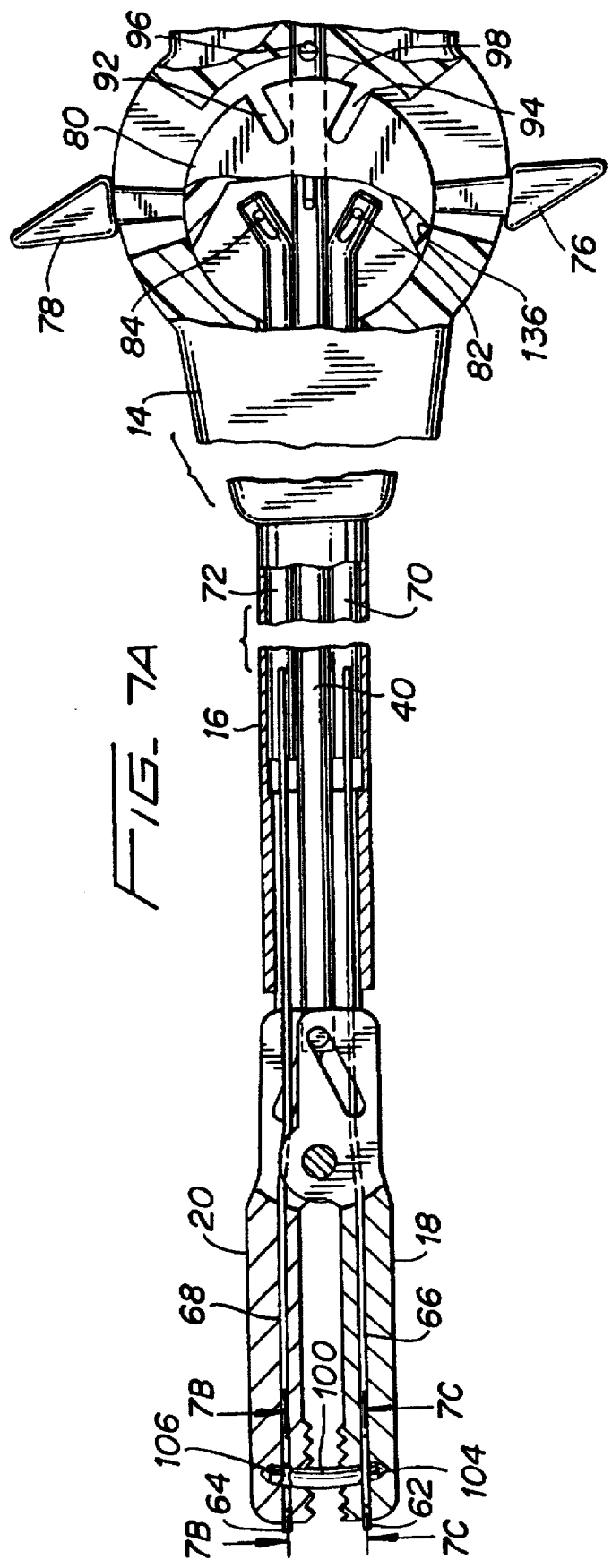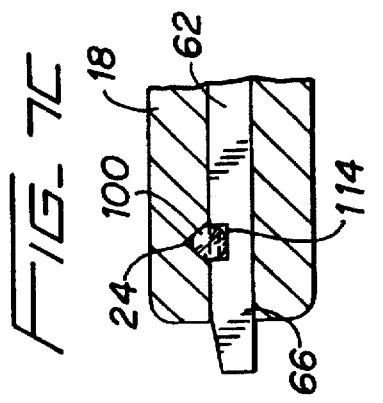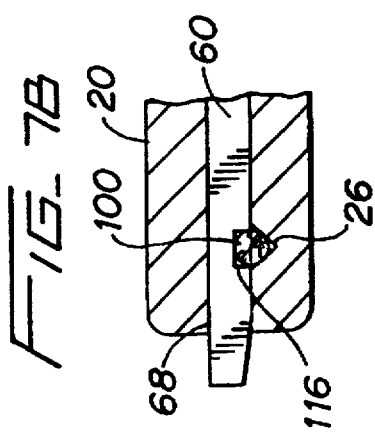

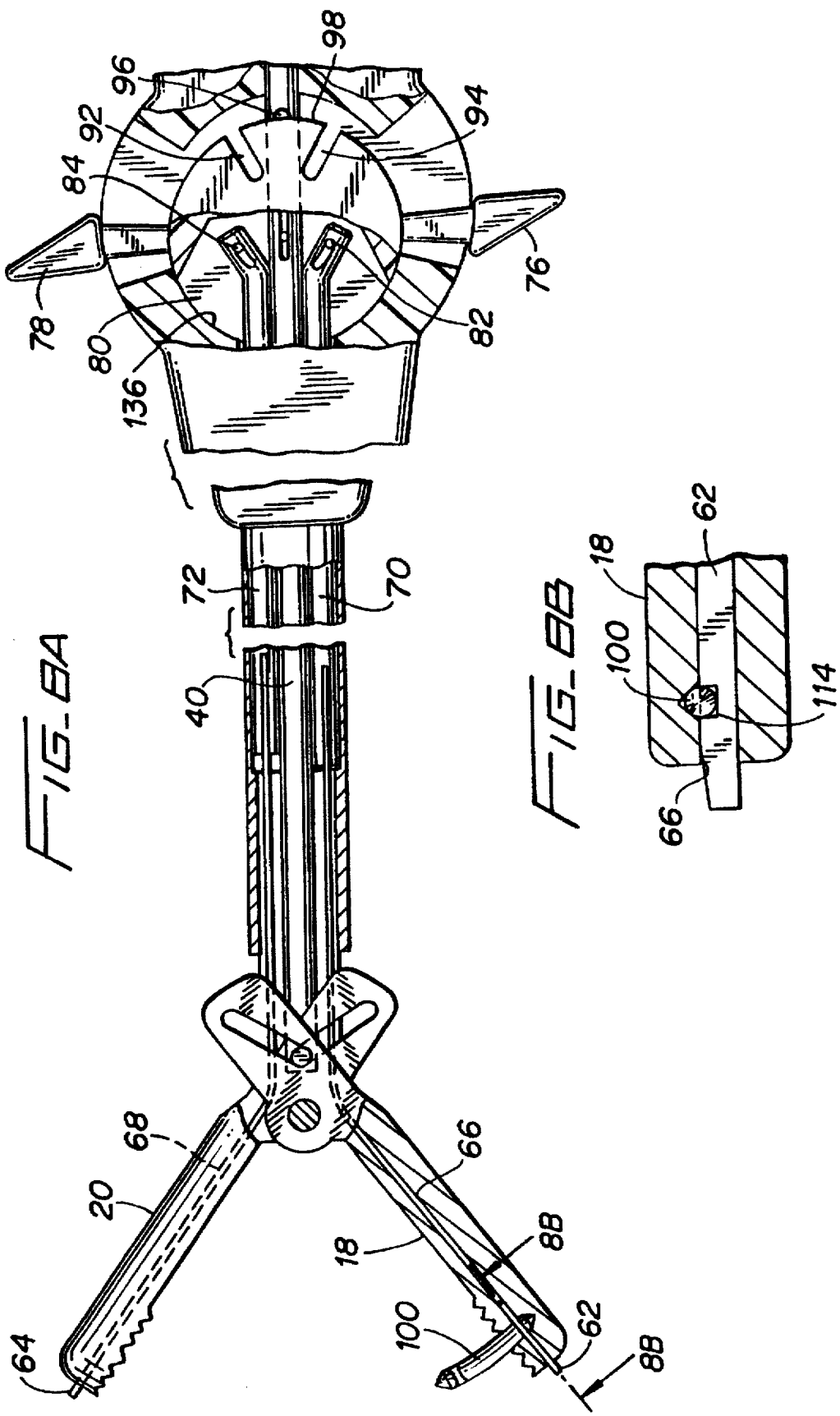

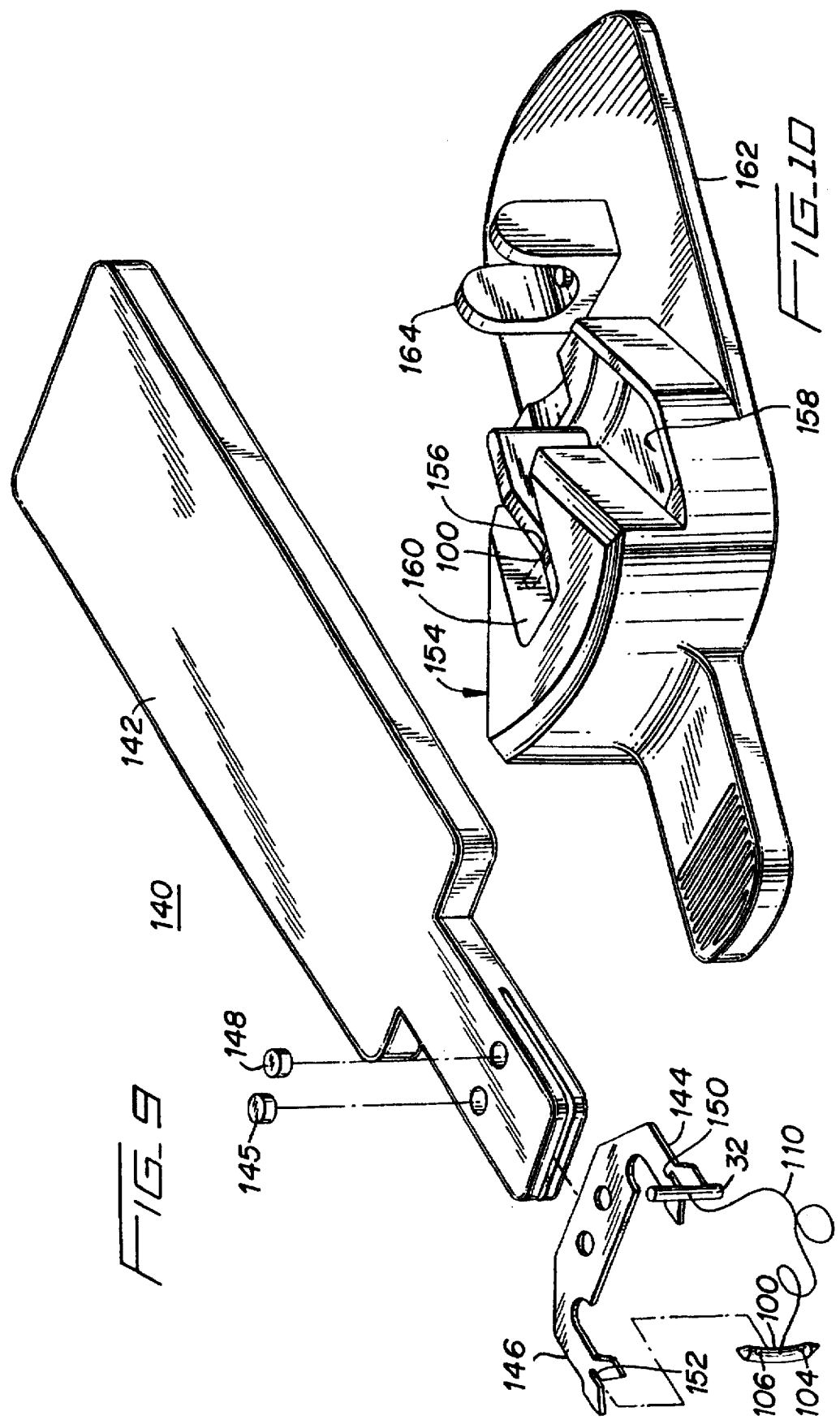

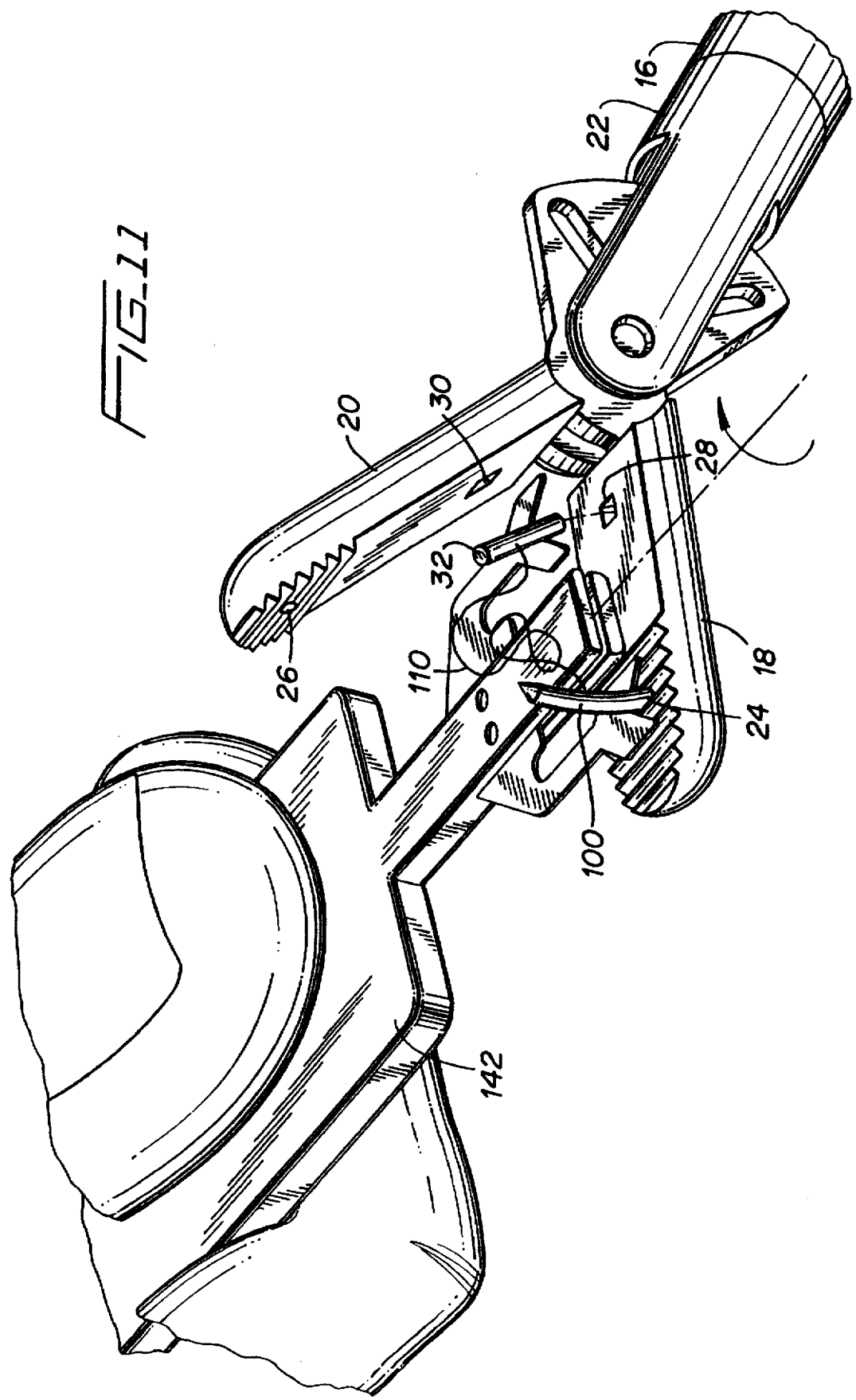

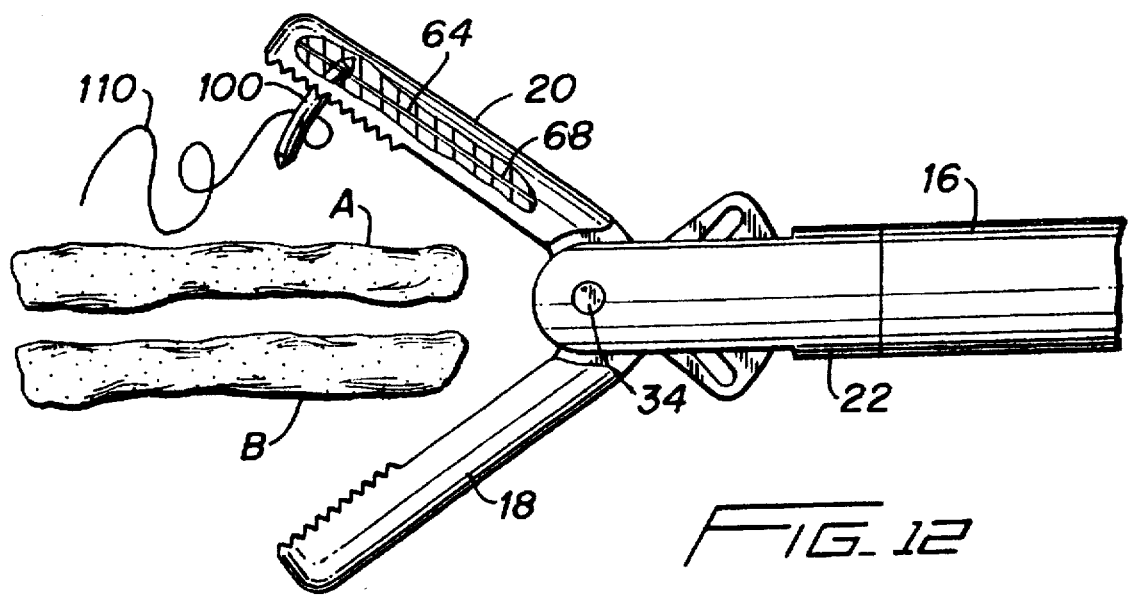
FIG_12
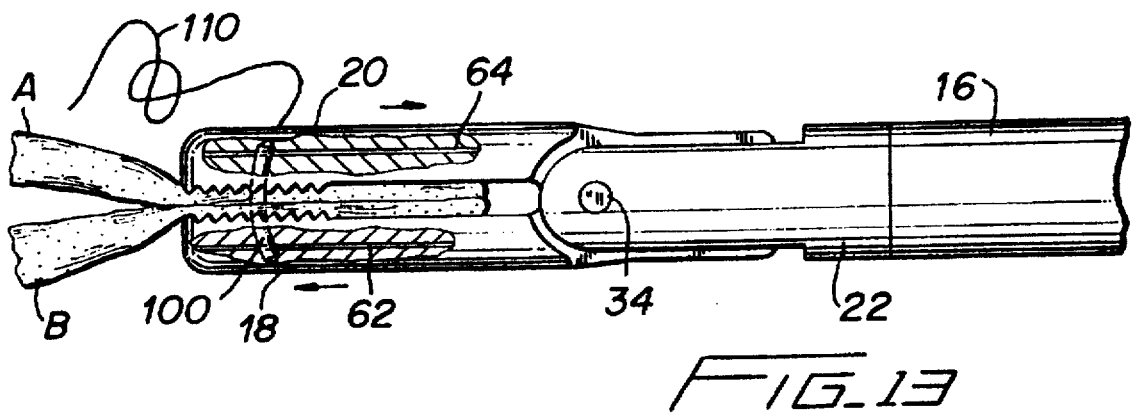
FIG_13
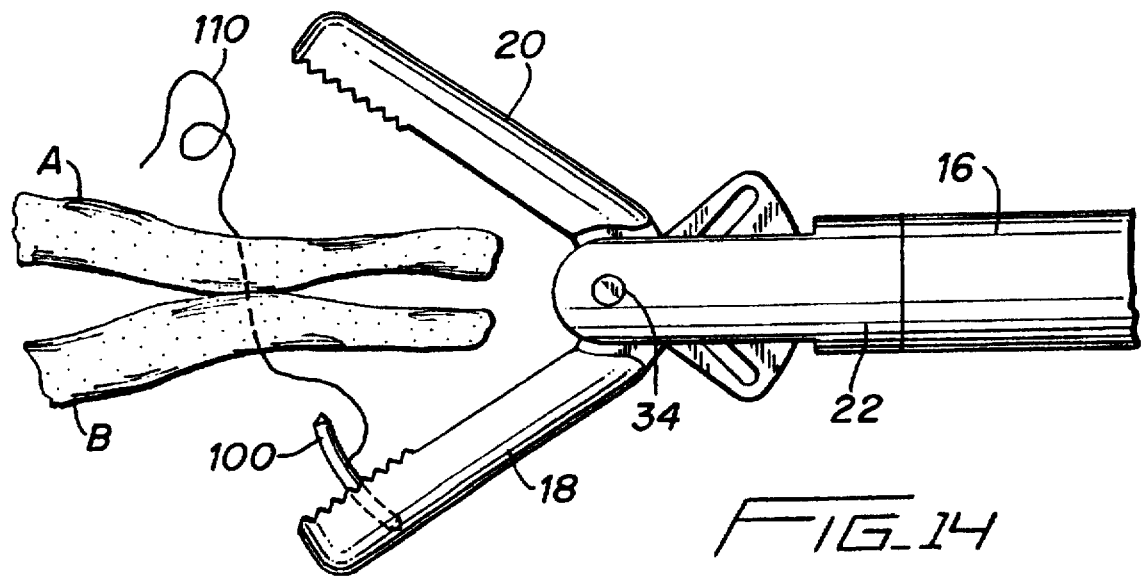
FIG_14

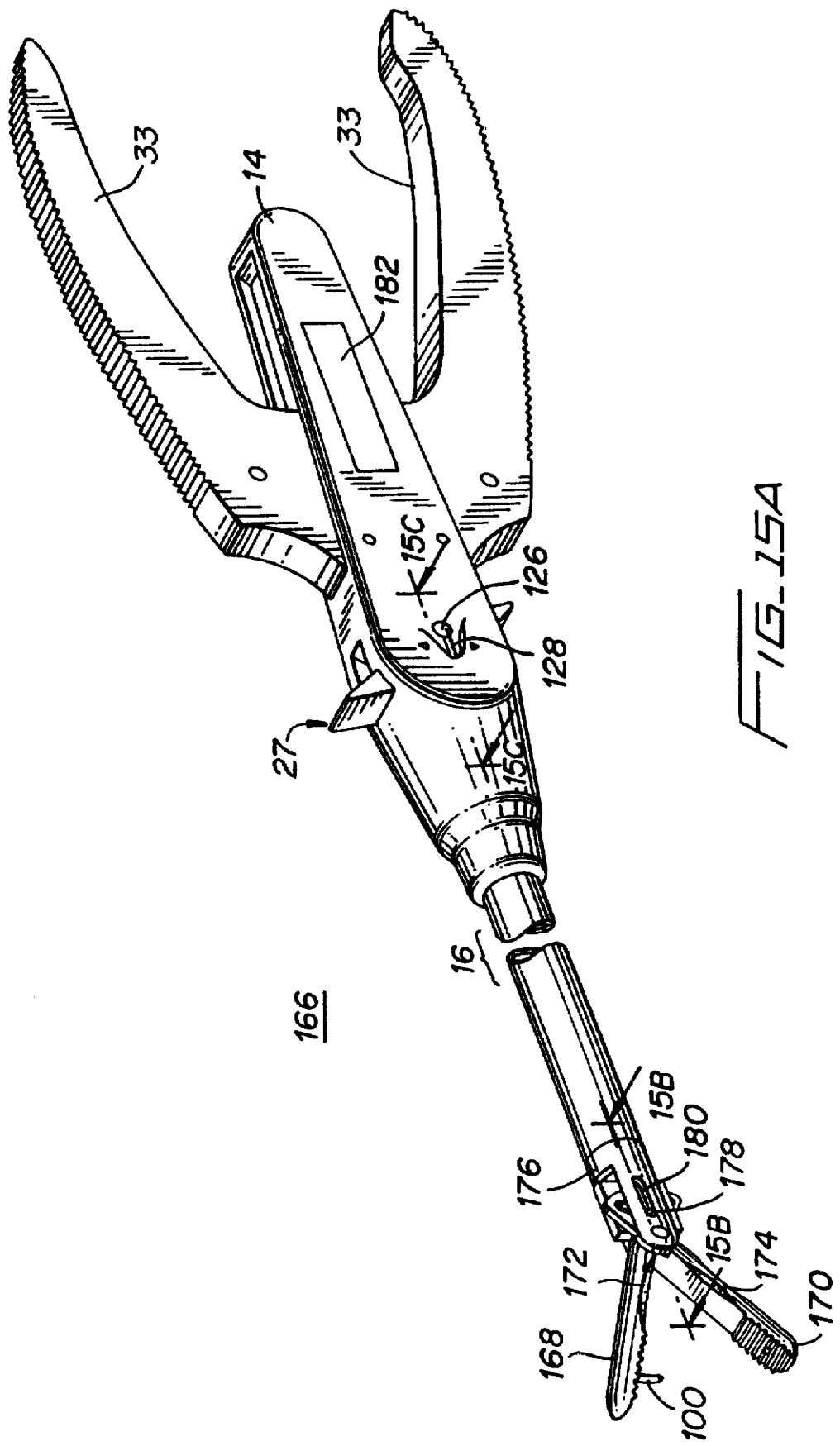

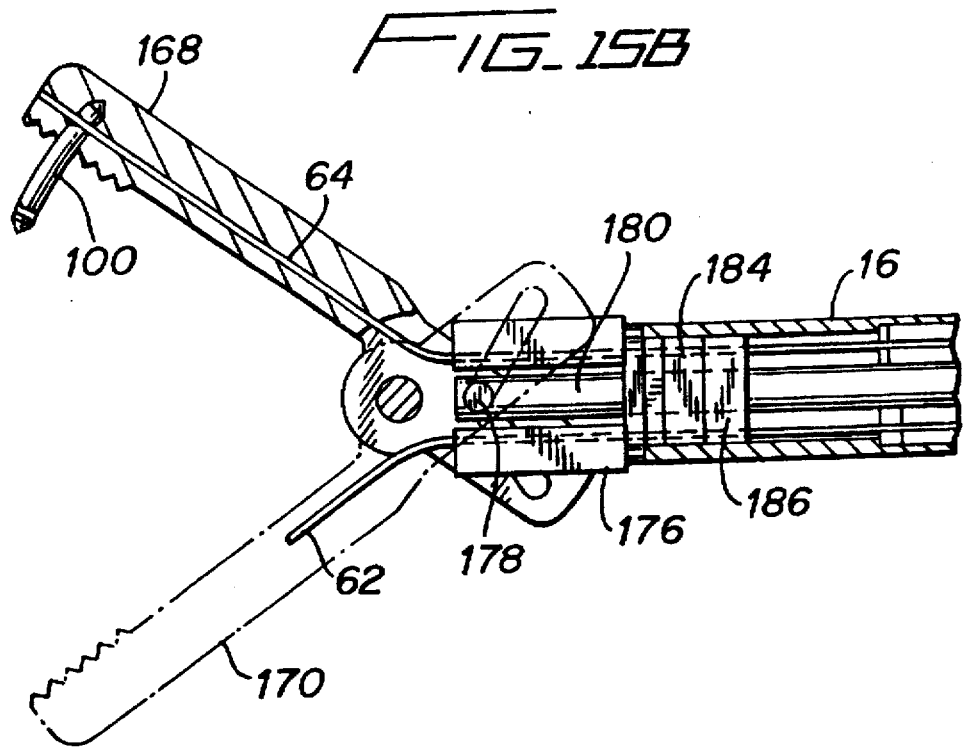
FIG_15B
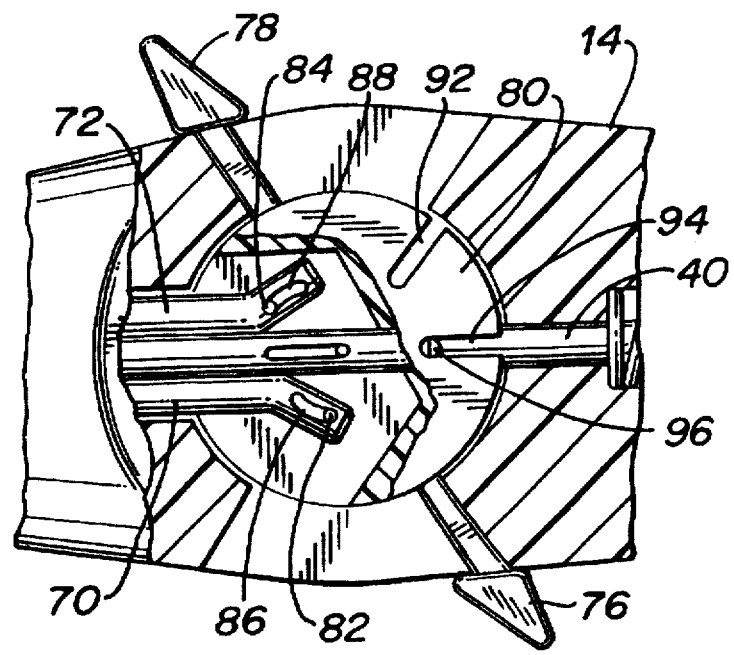
FIG_15C

FIG_15D
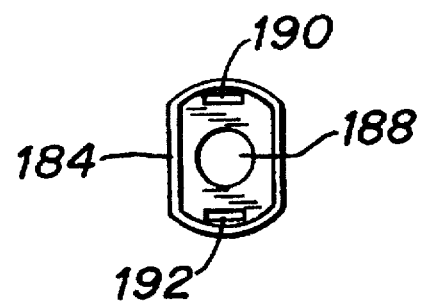
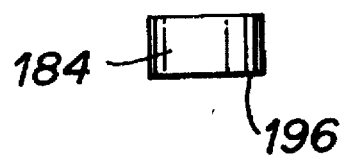
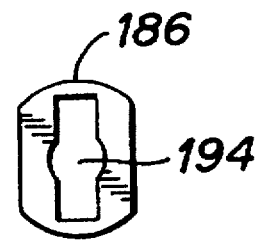

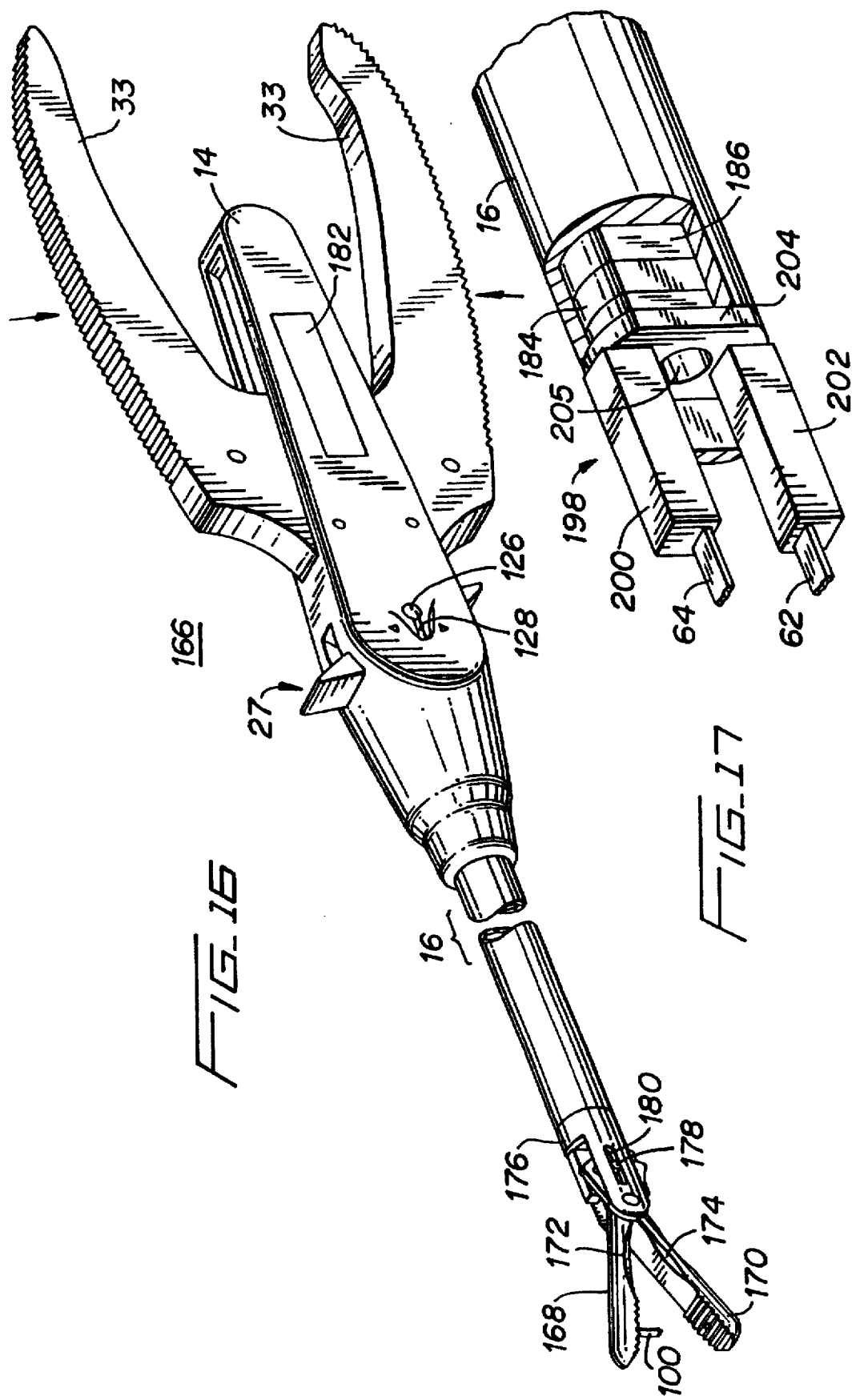

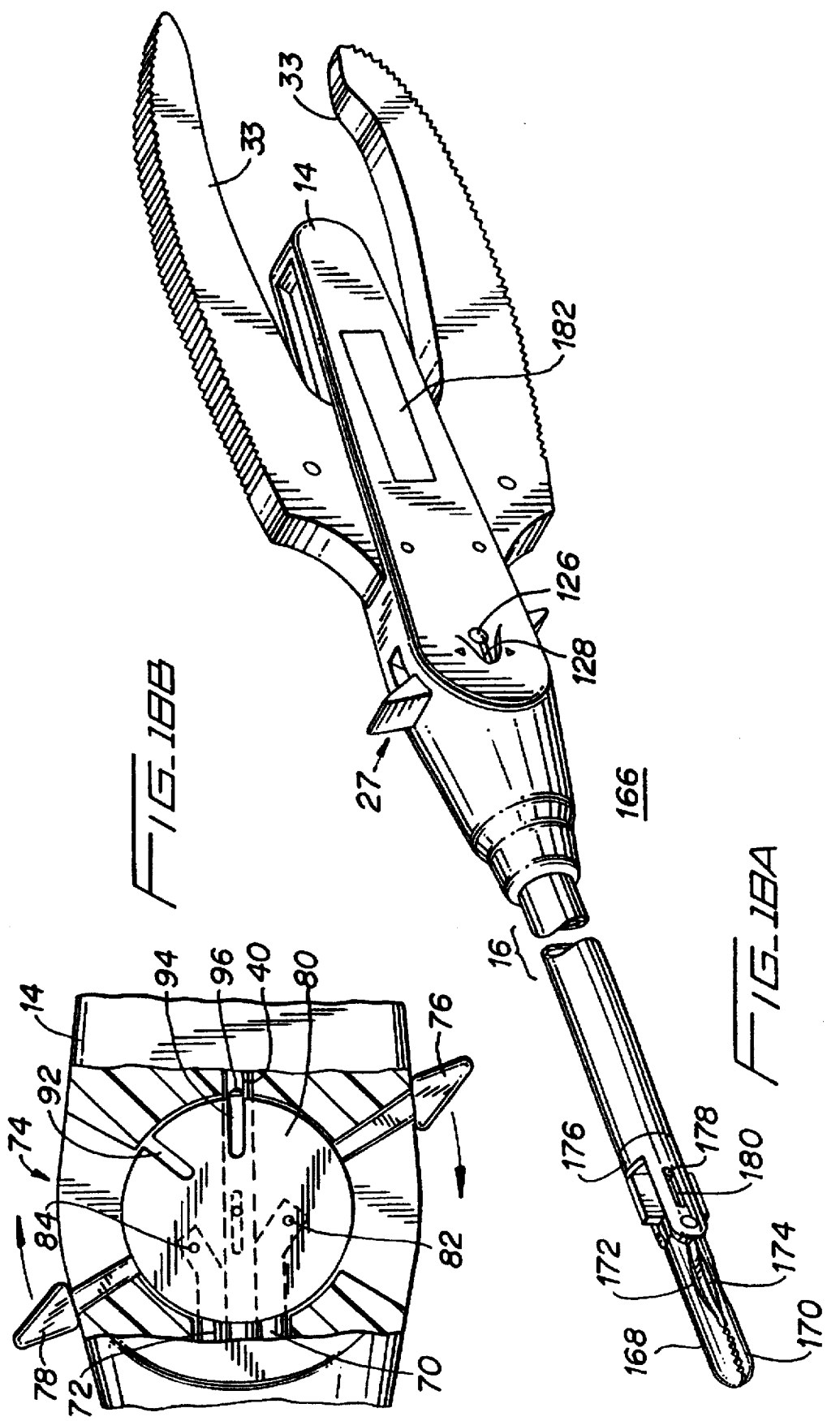

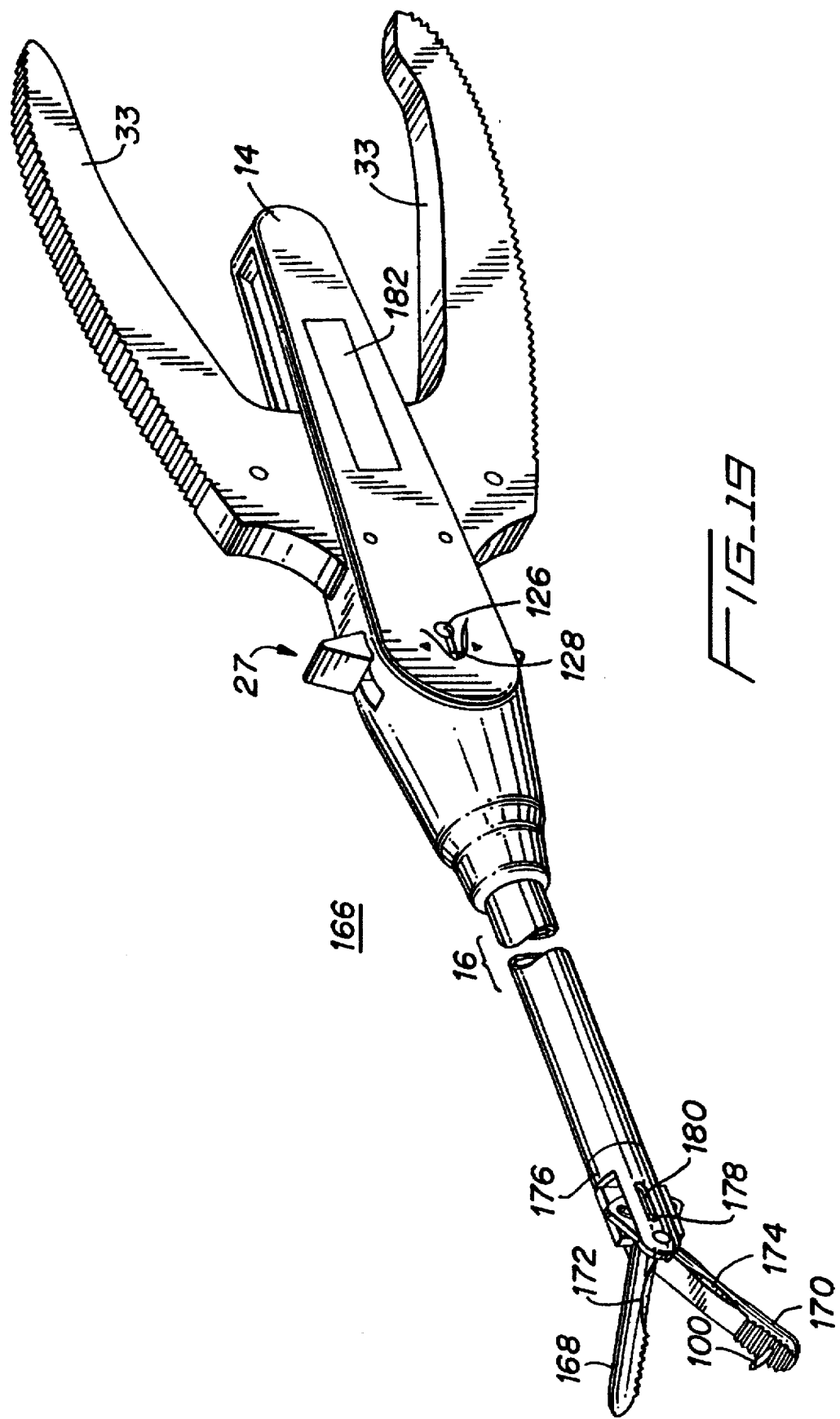

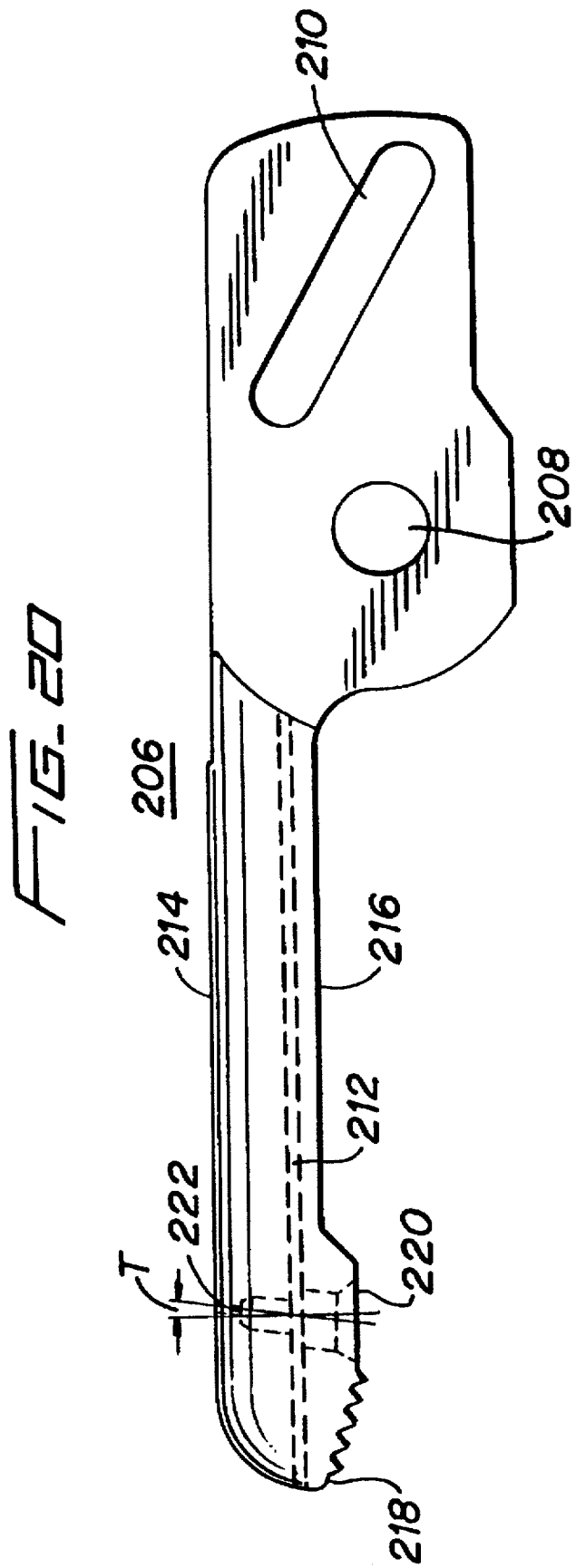

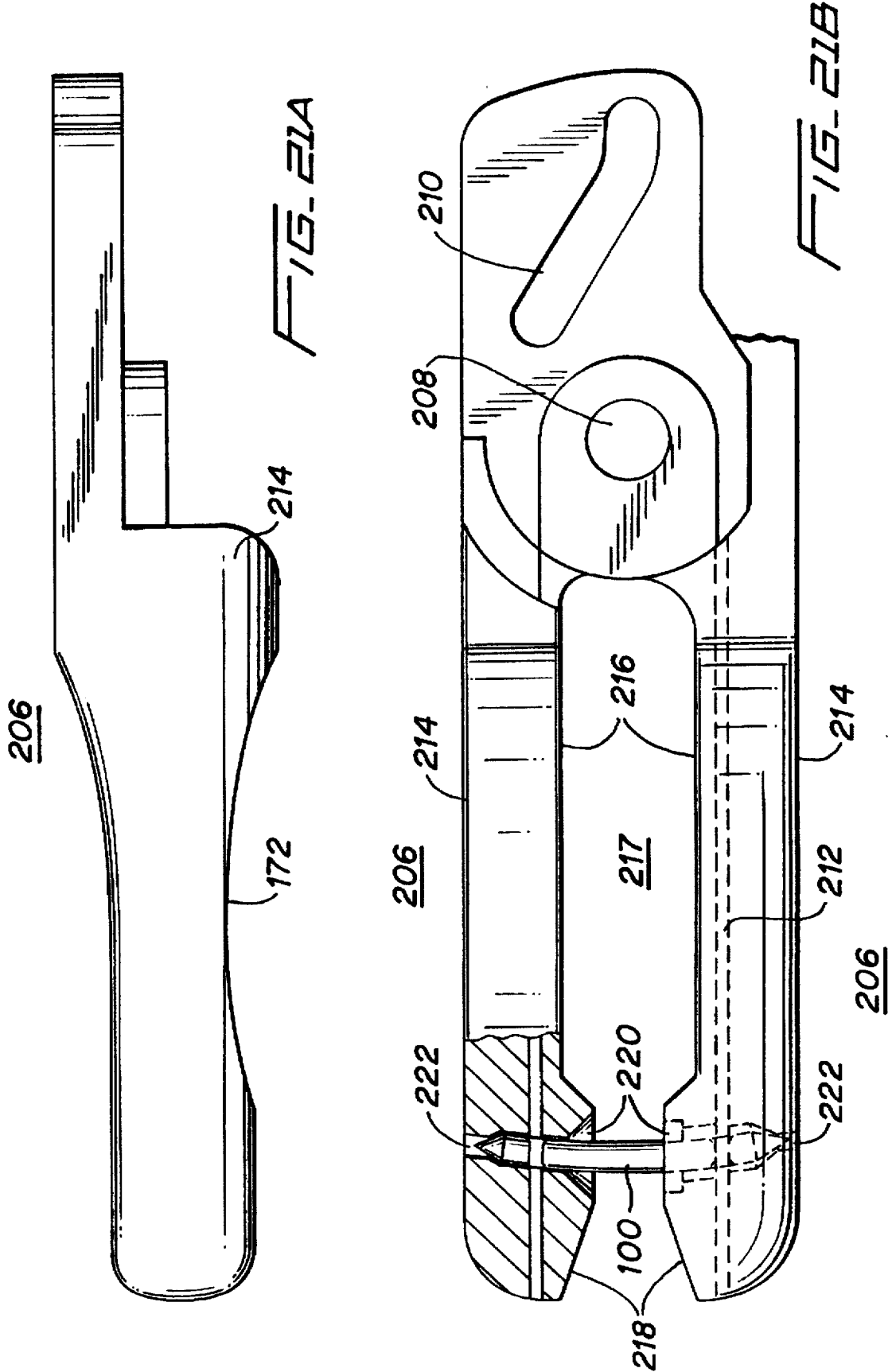

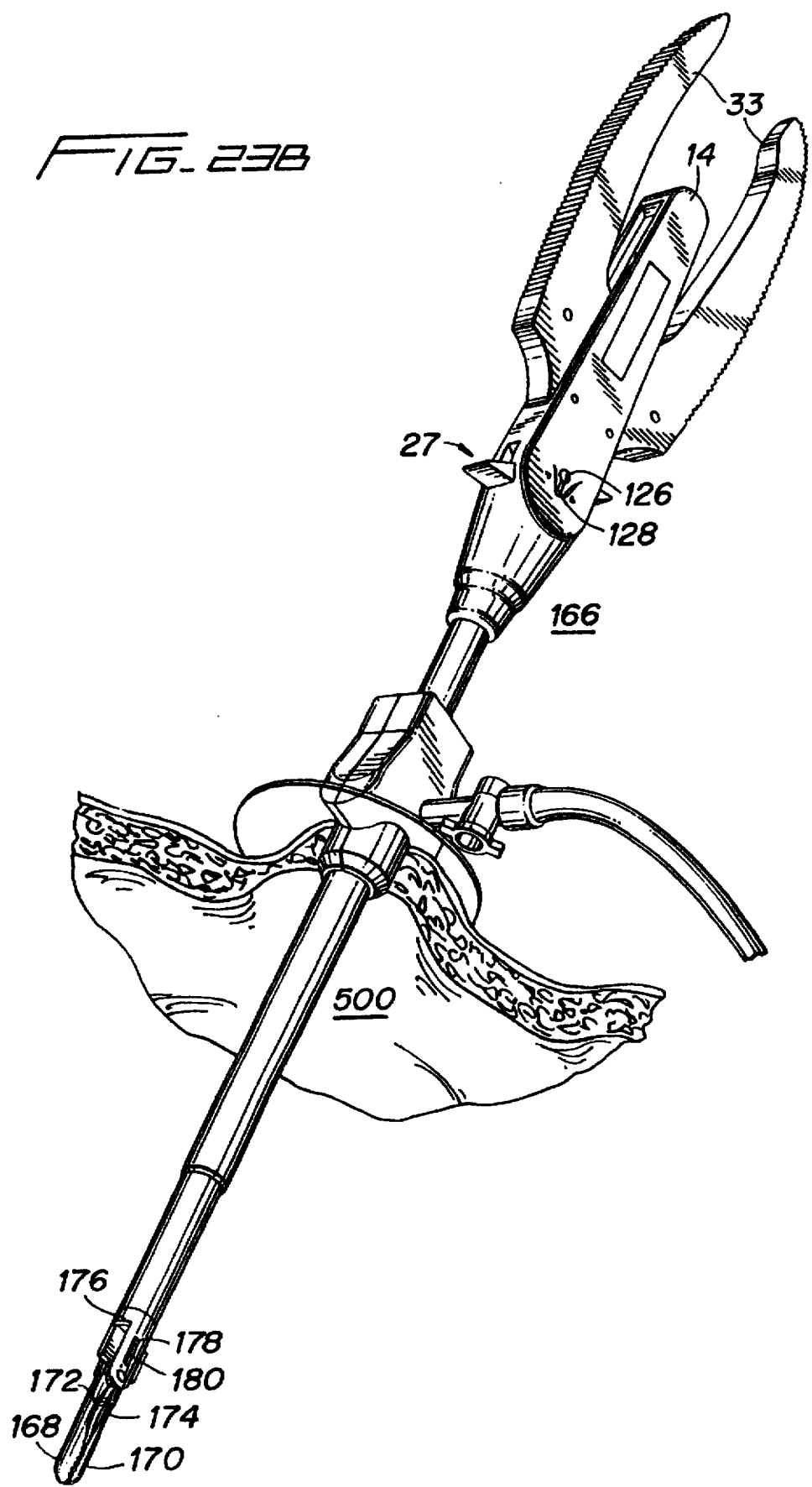

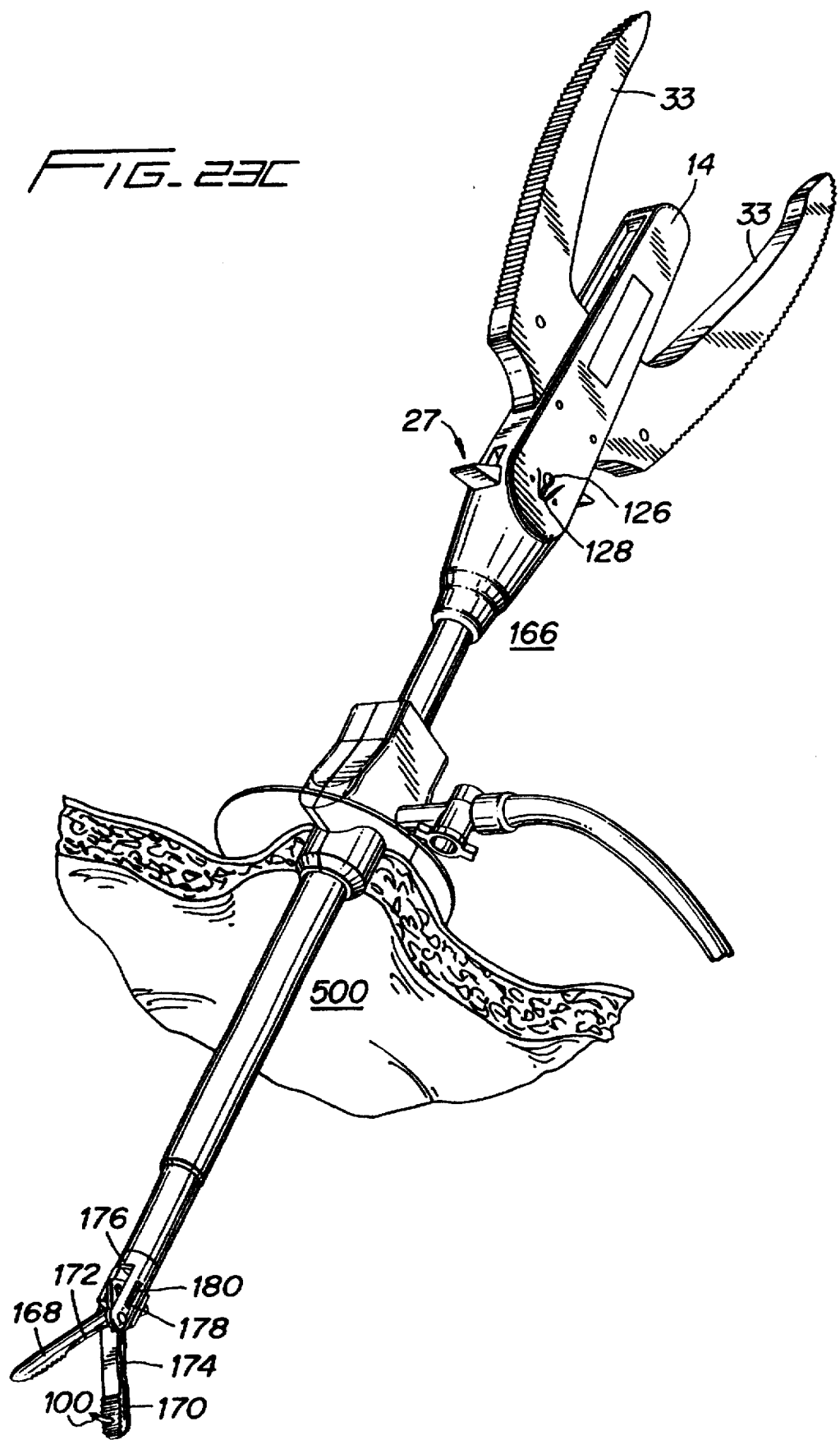

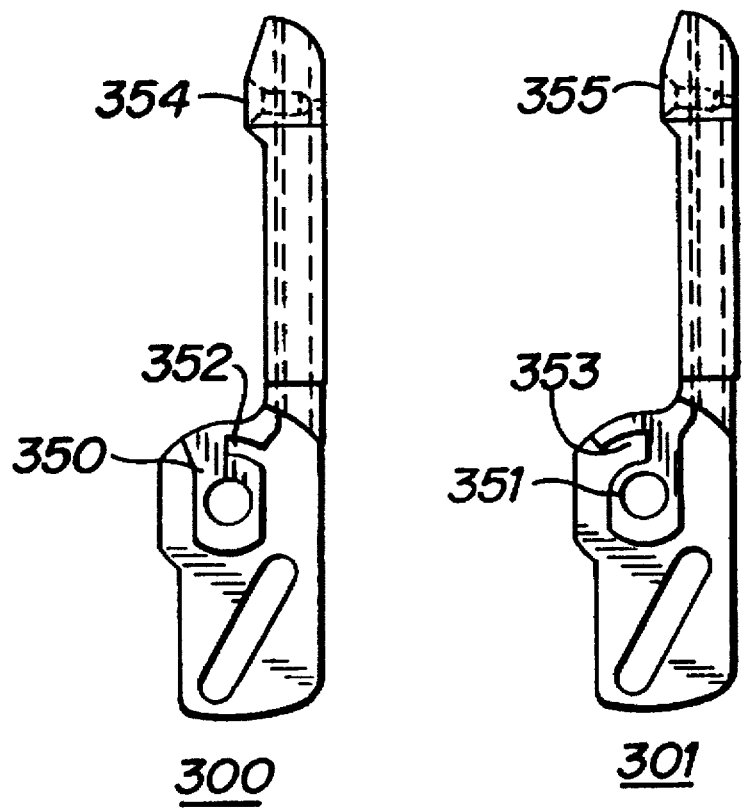

5,674,230

SURGICAL SUTURING APPARATUS WITH LOCKING MECHANISMS

RELATED APPLICATIONS

This application is a continuation of U.S. application Ser. No. 08/319,841 filed Oct. 7, 1994, now abandoned, which is a continuation-in-part of U.S. application Ser. No. 08/134,145 filed Oct. 8, 1993 now abandoned.

BACKGROUND

1. Technical Field

The technical field relates generally to surgical instrumentation and, more particularly, to a suturing apparatus suitable for use in endoscopic or laparoscopic surgical procedures.

2. Description of Related Art

During many surgical procedures in order to join tissue sections it is generally considered desirable to place two or three lines of stitching in the tissue sections, such as, for example, when performing an anastomosis to provide reinforcement. This is generally accomplished by providing a suturing device capable of passing a needle, having a length of suture material attached thereto, back and forth between jaws located on opposite sides of the tissues. One such device is disclosed in U.S. Pat. No. 4,236,470 to Stenson. The device of Stenson includes a pair of arms configured to alternately receive opposed ends of a needle-shuffle member. The shuttle member with an attached length of filament is passed alternately back and forth between the arms to stitch skin together.

Numerous surgical procedures are now being carried out endoscopically or laparoscopically. Endoscopic or laparoscopic procedures are characterized by the use of an elongated cannula having a relatively small diameter. The distal end of the cannula is passed through the surrounding tissue into the body cavity wherein the surgical procedure or examination is to be effected, thus providing a conduit for the insertion of surgical instrumentation. A plurality of cannulas may be used to allow insertion and operation of a variety of instruments simultaneously during a given procedure. For example, one cannula may provide a conduit for an endoscope for vision and illumination within the operative cavity while the other cannulas may provide conduits for control of specialized surgical instruments such as graspers, dissectors and staplers, designed for performing specific procedural functions.

During many endoscopic and laparoscopic procedures, it is necessary to rapidly and accurately place successive needle-suture combinations within the jaws of a surgical suturing apparatus for immediate and repeated use during the surgical procedure. Further, it is often necessary to hold the needles at specific locations along the needle body to facilitate suturing such as, for example, at one end or the other. Laparoscopic suturing presents a particularly challenging task, because it must be accomplished through a port that typically averages between five and ten millimeters. One instrument for facilitating laparoscopic suturing is discussed in British Patent Application No. 2260704, published Apr. 28, 1993.

Although the suturing device described in application Serial No. 2260704 can be used to place laparoscopic sutures, once the suture is used up, or if a new needle is required, the suturing device must be re-loaded by inserting the suture within the device by hand, which can be very time-consuming. As it is generally considered desirable to place two or three lines of stitching when performing an anastomosis to provide reinforcement, the laparoscopic suturing device as described in the British application mentioned above may require manual reloading one or more times.

Another instrument for facilitating laparoscopic suturing is disclosed in German Patent Specification No. DE 41 24 383 C1. The device disclosed in DE 41 24 383 C1 includes a stationary jaw having a spring biased needle clamping device and a movable jaw having a movable two part clamping device. A needle can be moved back and forth between the jaws by pushing or pulling the needle into or out of the rigid jaw with the movable jaw by way of pneumatic actuation. When the needle is retained within the movable jaw it is releasable at any time and when the needle is retained within the stationary jaw it cannot be released without being pulled free.

In the devices listed above the shuffle member or needle may be released from the jaws when the jaws are at least partially opened. Thus, the shuffle or needle may be lost resulting in inconvenience or, if released during surgery, potential injury to a patient. Additionally, as in the case of U.S. Pat. No. 4,236,470 and German Patent Specification No. DE 41 24 383 C1, the jaws of the device may be opened before the shuttle or needle has been fully secured therein resulting in the aforementioned dangers.

Thus, it would be advantageous to provide a laparoscopic suturing instrument to permit quick, efficient and safe reloading of a new needle and suture. A laparoscopic suturing device would also provide, an advantage if the surgical needle could not be released by the operator during a surgical operation while the jaws are in the open condition. It would be a further advantage if the jaws could be prevented from moving when the needle is not secured in either jaw, so as to prevent the needle from accidentally dislodging in the body cavity. It would be a still further advantage if the suturing device could be rapidly and precisely reloaded without touching the needle by hand.

SUMMARY

An apparatus for manipulating a surgical needle is disclosed, comprising a body portion, a first needle receiving jaw mounted for movement on a distal end of the body portion and having a first needle engaging member, a second needle receiving jaw mounted for movement on the distal end of the body portion and having a second needle engaging member, the second needle engaging member being operatively interconnected to the first needle engaging member for relative reciprocal movement therewith, wherein each of the first and second needle receiving jaws has a recess for receipt of a portion of a surgical needle therein. The first and second needle engaging members are mounted for alternate reciprocal movement into and out of locking engagement with the surgical needle. The apparatus also includes a wheel rotatably mounted within the body portion with a proximal end portion of each of the first and second needle engaging members connected to opposing sides of the wheel such that rotation of the wheel simultaneously retracts one of the needle engaging members and advances the other. Also includes is a pair of guide tubes which are disposed adjacent the body portion and around at least a portion of each of the needle engaging members to guide the needle engaging members during their reciprocal movement.

Also disclosed is a method of manipulating a surgical needle inside a body cavity comprising the steps of inserting a cannula into a body cavity, providing a surgical instrument having a control mechanism, a first jaw and a second jaw, at least one of the jaws being mounted for movement between a first position adjacent the other jaw and a second position spaced apart from the other jaw, inserting said jaws through the cannula into the body cavity, opening the jaws inside the body cavity to expose a pointed tip of the surgical needle secured in the first jaw, passing the surgical needle through the tissue to be sutured, and selectively and mechanically actuating the control mechanism to allow transfer of control of the needle from the first jaw to the second jaw.

BRIEF DESCRIPTION OF THE DRAWINGS

Various embodiments are described herein with reference to the drawings, wherein:

FIG. 2 is an exploded perspective view of the instrument depicted in FIG. 1;

FIG. 2A is an enlarged view of a portion of FIG. 2 illustrating the wheel mechanism.

FIG. 2B is a side cross-sectional view of a portion of the mechanism that overrides the lockout mechanism of the instrument depicted in FIG. 1;

FIG. 3 is an exploded perspective view of the distal end of the instrument depicted in FIG. 1;

FIG. 4A is an enlarged plan view in partial cross-section of a portion of the instrument depicted in FIG. 4;

FIG. 4B is a cross-sectional view taken along line 4B—4B of FIG. 4A;

FIG. 4C is a plan view in partial cross-section of the surgical needle;

FIG. 4D is a perspective view of the surgical needle, surgical suture thread and suture anchor;

FIG. 5 is a plan view in partial cross-section showing the instrument depicted in FIG. 1 with the jaws closed and the toggle wheel positioned to retain the needle in the lower jaw;

FIG. 5A is an enlarged plan view in partial cross-section of a portion of the instrument depicted in FIG. 5;

FIG. 5B is a cross-sectional view taken along the line 5B—5B of FIG. 5A;

FIG. 5C is a cross-sectional view taken along the line 5C—5C of FIG. 5A;

FIG. 5D is an enlarged cross-sectional view of a portion of the center rod and the lock pin taken along line 5D—5D of FIG. 5A;

FIG. 6A is an enlarged plan view in partial cross-section similar to FIG. 4A of a portion of the instrument showing the jaws in the open position and the surgical needle retained in one jaw;

FIG. 6B is a cross-sectional view taken along the line 6B—6B of FIG. 6A;

FIG. 7A is an enlarged plan view in partial cross-section of a portion of the instrument depicted in FIG. 1 showing the lockout override mechanism activated with the jaws in the closed position;

FIG. 7B is a cross-sectional view taken along the line 7B—7B of FIG. 7A;

FIG. 7C is a cross-sectional view taken along the line 7C—7C of FIG. 7A;

FIG. 8A is an enlarged plan view in partial cross-section of a portion of the instrument depicted in FIG. 1 with the lockout override mechanism activated and the jaws in the open position;

FIG. 8B is a cross-sectional view taken along the line 8B—8B of FIG. 8A;

FIG. 9 is a perspective exploded view of one embodiment of a loading mechanism for the surgical suturing apparatus of FIG. 1;

FIG. 10 is a perspective view of an alternate embodiment of a loading mechanism;

FIG. 11 is a perspective view showing the jaws of the apparatus of FIG. 1 being placed into the loading mechanism of FIG. 9;

FIGS. 12, 13 and 14 show a plan view in partial cross-section of the jaws of the instrument as they pass the surgical needle therebetween and draw the surgical needle and connected length of suture material through a pair of tissue sections;

FIG. 15A is a perspective view of an alternate embodiment of the surgical suturing apparatus;

FIG. 15B is an enlarged cross-sectional plan view of the jaw portion of the instrument taken along the line 15B—15B of FIG. 15A with the jaws in an open condition;

FIG. 15C is an enlarged cross-sectional plan view taken along the line 15C—15C of FIG. 15A;

FIG. 15D shows end and side views of a seal and guide assembly illustrated in FIG. 15B;

FIG. 16 is a perspective view of the instrument depicted in FIG. 15A with the jaws in a partially open position;

FIG. 17 is an enlarged perspective view of a blade guide assembly;

FIG. 18A is a perspective view of the instrument depicted in FIG. 15A with the jaws in a closed position;

FIG. 18B is an enlarged view, partially shown in section, of the wheel and lock pin position corresponding to FIG. 15A;

FIG. 19 is a perspective view similar to FIG. 15A with the surgical needle retained in the lower jaw;

FIG. 20 is an enlarged plan view of an alternate embodiment of the jaw for use in the surgical instruments depicted in FIGS. 1 and 15A;

FIGS. 21A and 21B are enlarged top plan and side plan views, respectively, of the jaw of FIG. 20;

FIG. 23B is a perspective view of the instrument of FIGS. 1 and 15A with the jaws closed, placed in a trocar in a body cavity;

FIG. 23C is a perspective view of the instrument of FIGS. 1 and 15A with the jaws open, placed in a trocar in a body cavity; and FIG. 24 is an enlarged plan view of an alternate embodiment of a pair of jaws for use in the surgical instruments depicted in FIGS. 1 and 15A.

DESCRIPTION OF PREFERRED EMBODIMENTS

Figure 1:
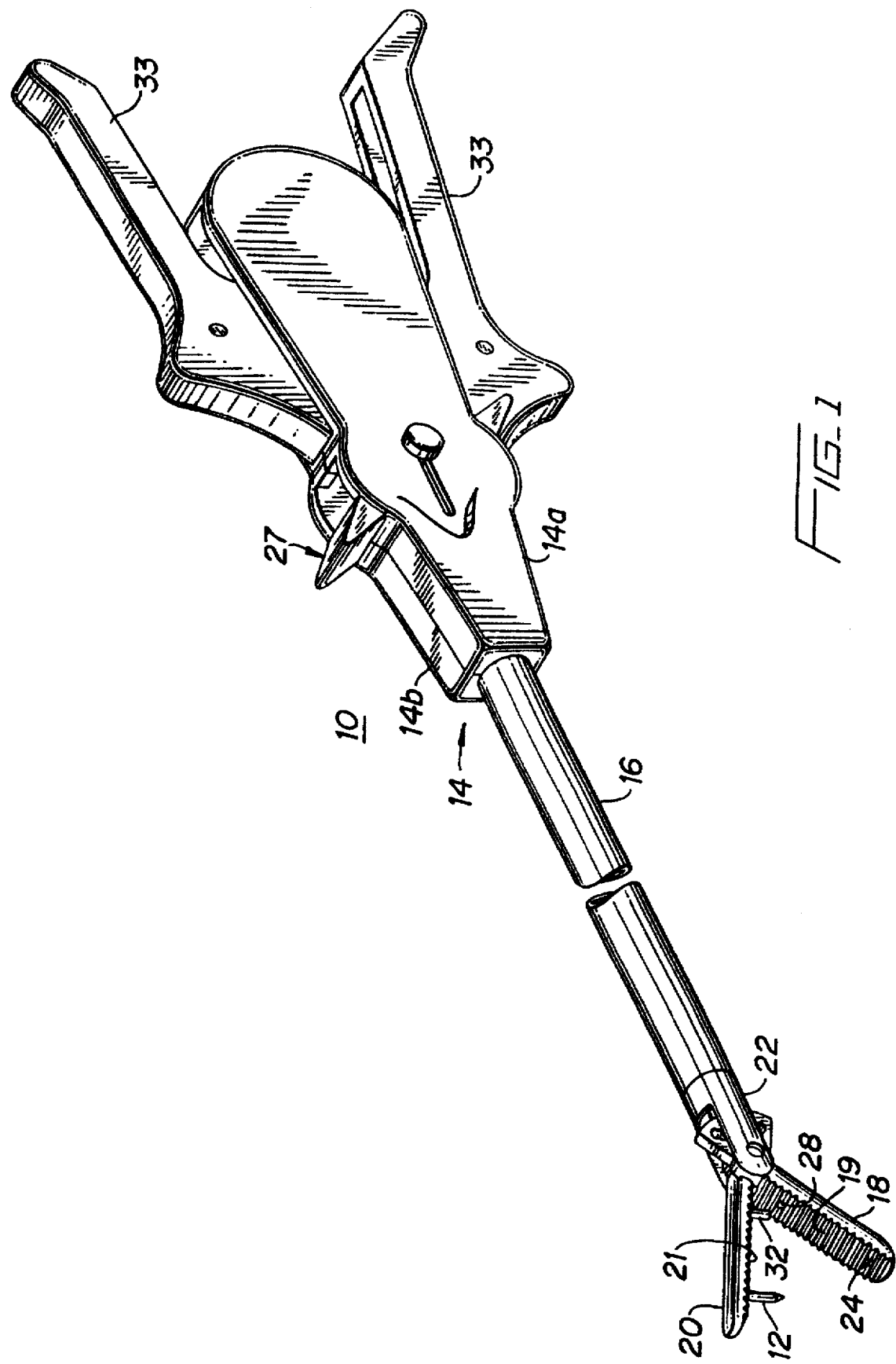
FIG. 1 is a perspective view of one embodiment of the surgical suturing apparatus.

Referring to FIG. 1, there is illustrated a surgical suturing apparatus 10 which is particularly suited to repeatedly pass a double pointed surgical needle or surgical incision member 12 back and forth between a pair of jaws mounted on a distal end of apparatus 10. As used herein, the term "surgical needle" refers genetically to all types of surgical needles while the term "surgical incision member" is directed more generically to any object that can be used with a surgical suturing apparatus to suture tissue, including single or double-pointed surgical needles or a stiffened portion of surgical suture. While apparatus 10 may employ any type of surgical incision member, apparatus 10 is specifically designed to hold double pointed surgical needle 12 within the jaws when the jaws are in a closed position and to lock surgical needle 12 into one of the jaws when the jaws are moved to an open position thereby maintaining control of surgical needle 12 during an entire suturing operation.

Surgical suturing apparatus 10 generally includes a handle housing 14, having housing halves 14a and 14b, and an elongated tubular housing or body portion 16 extending distally from the handle housing 14. A pair of needle receiving jaws 18 and 20 are pivotally mounted with respect to body portion 16 and are mounted for movement between an open position spaced apart from each other and a closed position wherein jaws 18 and 20 are in close cooperative alignment for gasping the tissue sections to be sutured and passing surgical needle 12 between them. Preferably jaws 18 and 20 have tissue engaging surfaces 19 and 21, respectively, which may be ridged along their entire length, only a portion thereof or not at all. Jaws 18 and 20 are preferably mounted for pivotal movement on a jaw support member 22 which is affixed to a distal end of housing 16.

As noted above, jaws 18 and 20 are each designed to secure surgical needle 12 therein. Jaws 18 and 20 include needle receiving recesses 24 and 26 (FIG. 3) respectively, which are configured to surround and hold at least a portion of the surgical needle 12 disposed therein substantially perpendicular to tissue engaging surfaces 19 and 21. Needle receiving recesses 24 and 26 may have various cross sectional shapes, such as, for example, square, rectangular, diamond shaped, etc., and preferably are of circular cross-section.

Securing mechanism 27, which is shown in FIG. 2 and is described in detail below, secures surgical needle 12 within either of the recesses 24 and 26 in jaws 18 and 20, respectively, thereby locking needle 12 within one of jaws 18 and 20 when the jaws are in an open position. Wheel 80 selectively controls the securing mechanism in a manner described below. Thus, apparatus 10 enables the passage of the surgical needle between the jaws to remotely suture body tissue.

The Jaw and Handle Mechanisms

Surgical suturing apparatus 10 includes a handle with two arms 33 designed to move jaws 18 and 20 between an open position spaced apart from each other to a closed position wherein the tips of jaws 18 and 20 are in close cooperative alignment. Handles 33 may be designed to move in the same plane as jaws 18 and 20 to provide an ergonomic advantage. Additionally, housing 14 may also be rotatably connected to body portion 16 to provide a further ergonomic advantage. This embodiment of the surgical suturing apparatus is particularly well adapted for use in endoscopic or laparoscopic procedures as tubular body portion 16 is preferably dimensioned to be insertable into a tubular cannula or trocar having an internal diameter of five to ten millimeters.

Referring now to FIGS. 2 and 3, jaws 18 and 20 are pivotally mounted on support member 22 by means of a jaw pivot pin 34 which extends through holes 36 in support member 22 and pivot holes 38 in each of jaw members 18 and 20. To move jaws 18 and 20 between an open position and a closed position there is provided an axially or longitudinally moveable center rod 40 having a camming pin 42 mounted at a distal end 44 thereof. Camming pin 42 rides in and engages angled camming slots 46 and 48 in jaws 18 and 20, respectively, such that distal movement of center rod 40 causes jaws 18 and 20 to be cammed into an open position and proximal movement of center rod 40 causes jaws 18 and 20 to be cammed into the closed position.

As defined herein, "distal" refers to the portion of the instrument remote from the user. "Proximal" refers to the portion of the instrument closer to the user.

Figure 4:
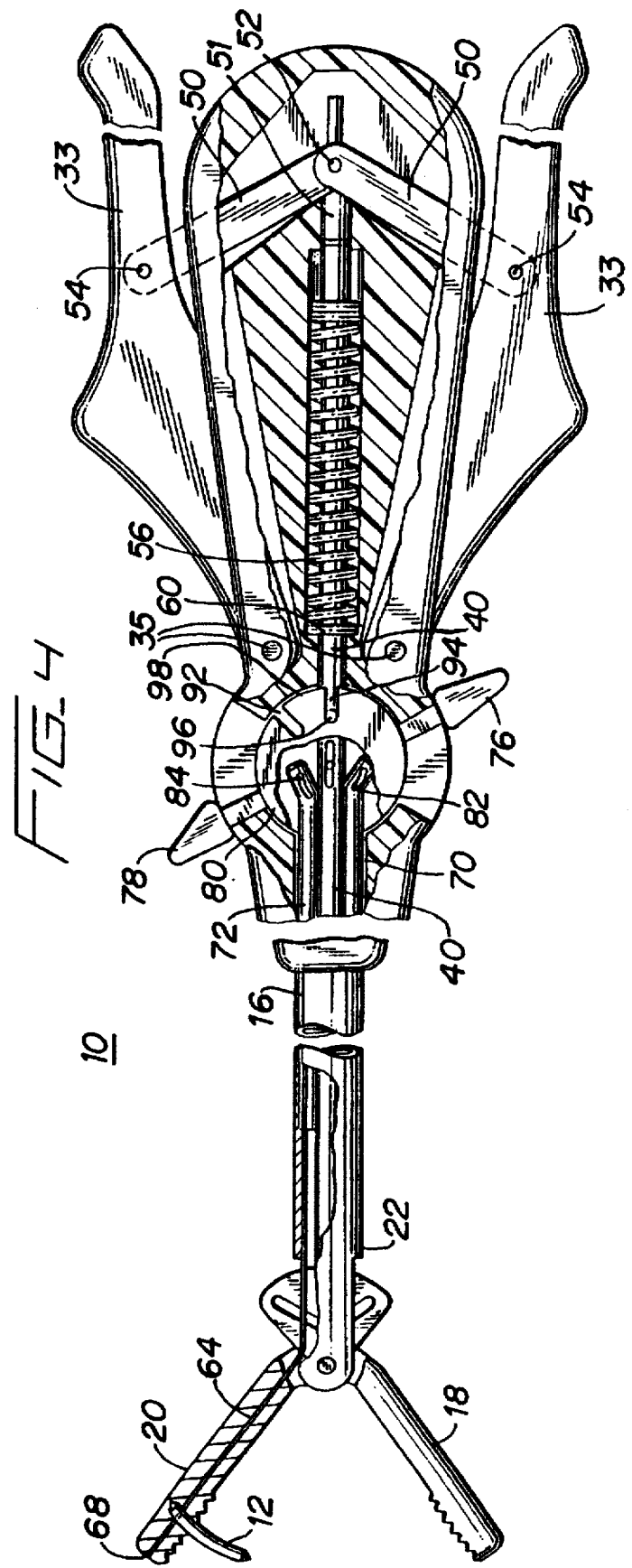
FIG. 4 is a plan view in partial cross-section showing the instrument depicted in FIG. 1 with the jaws open and a surgical needle secured in the upper jaw.

Referring now to FIGS. 2 and 4, handles 33 are connected to center rod 40 by a parallel pair of links 50 which are pinned to a proximal end 51 of center rod 40 by pins 52. The opposite ends of links 50 are connected to handles 33 by means of pins 54. Handles 33 are pivotally connected to housing halves 14a and 14b by pivot pins 35. Thus, closing handles 33 toward handle housing 14 drives links 50, and thus center rod 40, proximally, thereby camming jaws 18 and 20 to a closed position, while opening handles 33 causes jaws 18 and 20 to be cammed into the open position. Handles 33 therefore permit manual, mechanical actuation to open and close jaws 18 and 20.

During certain surgical operations it is preferable that the jaws of suturing apparatus 10 be biased to an open position thereby requiring the operator to squeeze handles 33 together to move jaws 18 and 20 to a closed position. Thus there is provided a jaw biasing spring 56 which resides in a channel 58 formed between housing halves 14a and 14b. Spring 56 is disposed around center rod 40 and abuts a spring washer 60 affixed to center rod 40.

Preferably, surgical suturing apparatus 10 is provided with a combined seal and rod guide 90 disposed within a distal end of body portion 16. Guide 90 has a channel 91 therein for guidance and support of center rod 40, a pair of blades 62 and 64 and side rods 70 and 72, described below, during their axial movement.

Referring now to FIGS. 4, 4a and 4b, in an initial state (FIGS. 4 and 4a), spring 56 is in a partially compressed state biasing handles 33 to an open position through links 50 and maintaining center rod 40 at a distalmost position within tube 16. Thus camming pin 42 is in a distalmost position to bias jaws 18 and 20 in an open position. Referring to FIGS. 5 and 5a, upon closure of handles 33, links 50 drive center rod 40 proximally, thereby further compressing spring 56 between spring washer 60 and an edge 61 of handle housing 14 (FIG. 2A), and thus drawing camming pin 42 proximally to cam jaws 18 and 20 to a closed position.

The Securing Mechanism

As noted above, surgical suturing apparatus 10 is designed to secure a surgical needle within one of recesses 24 or 26 in jaws 18 or 20, respectively, when jaws 18 and 20 are in the open position. Referring now to FIGS. 2, 3 and 4a, securing mechanism 27 generally includes a pair of needle engaging members or blades 62 and 64 which are slidably mounted within blade channels 66 and 68 in jaws 18 and 20, respectively. Channels 66 and 68 are dimensioned and configured so as to at least partially intersect needle recesses 24 and 26. Thus, by advancing blade 62 or 64 within channels 66 and 68, the advanced blade engages or "locks in" surgical needle 12 disposed within the respective recess 24, 26. These recesses are preferably offset to one side of the jaws 18 and 20. A pair of side rods 70, 72 which are mounted for axial movement within body portion 16 and adjacent center rod 40 move blades 62 and 64 within jaws 18 and 20. Surgical needle 12 is secured within only one of jaws 18 and 20 at a time, thus when one blade, such as, for example, blade 64, is advanced to engage or "lock in" surgical needle 12 in jaw 20, the opposing blade 62 will alternately be retracted to a position disassociated with recess 24, thus releasing surgical needle 12 from jaw 18 so it may be transferred to jaw 20.

Referring now to FIGS. 4 and 4a, in order to alternately advance and retract blades 62 and 64 there is provided a reciprocating mechanism 74 which is configured to reciprocally move side rods 70 and 72 and thus blades 62 and 64. Reciprocating mechanism 74 generally includes a pair of control arms 76 and 78 which are affixed to a wheel 80 rotatably mounted with respect to housing 14. Wheel 80 has a pair of drive pins 82 and 84 which attach the distal ends of side rods 70, 72 respectively, to wheel 80. Referring to FIGS. 4, 4a, 4b, 5 and 5a, as arm 78 is moved distally and arm 76 is moved proximally, wheel 80 rotates and pin 84 moves rod 72 distally, thereby driving side rod 72 and thus blade 64 distally into engagement with the surgical needle. At the same time, pin 82 and side rod 70 are drawn proximally, thereby drawing blade 62 out of recess 24. As shown in FIG. 5a, upon drawing arm 78 proximally and advancing arm 76 distally, side rods 72, 70 are caused to alternately move in the proximal and distal directions, respectively, due to the attachment of side rods 70 and 72 to wheel 80 by virtue of pins 84, 82. In this manner reciprocating control mechanism 74 operates to alternately cause blades 62, 64 to intersect or move away from needle recesses 24, 26, respectively, and thus alternately engage and disengage surgical needle 12 disposed therein. Reciprocating mechanism therefore allows the operator to manually, mechanically, selectively actuate the transfer of a needle from jaw 18 to jaw 20 and vice versa. It should be noted that the same hand used to squeeze handles 33 may be used to move reciprocating mechanism 74, i.e., a surgeon could squeeze the handles between the thumb and index finger on one hand, and could actuate reciprocating mechanism with that same forefinger while maintaining control over the handles with the thumb and remaining three fingers.

The Surgical Incision Member

Referring to FIG. 4C, there is disclosed a particularly suitable surgical needle 100 for use with surgical suturing apparatus 10. Surgical needle 100 is preferably disclosed in more detail in U.S. patent application Ser. No. 08/131,145 filed Oct. 8, 1993 and Ser. No. 08/260,579 filed Jun. 16, 1994. Surgical needle 100 is preferably a double ended surgical needle having pointed ends 102 and a pair of engagement recesses 104 and 106 which are positioned adjacent each end 102. Surgical needle 100 may be provided with a suture receiving hole 108 which is designed to retain a portion of an associated length of surgical suture material 110. To retain suture material 110 within needle 100, suture material 110 may be either glued into channel 108, needle 100 may be crimped about suture material 110 or suture material may be looped through a recess in needle 100, making the "loop" portion of the suture half as thick as the "tail" portion of suture to prevent a double thickness of suture at the point of attachment with needle 100. Preferably surgical needle 100 includes a recess or scalloped area 112 which allows a portion of suture material 110 to lie flush against surgical needle 100 as it is repeatedly passed through tissue sections. Preferably surgical needle 100 is arcuate and has a radius substantially equal to the distance between needle recesses 24, 26 and pivot pin 34, as seen in FIG. 5. Additionally, surgical needle 100 may have various cross-sections, such as, for example, rectangular, triangular, etc., although a circular cross-section is preferred.

In an alternate embodiment, as shown in FIG. 4d, an opposing end of suture material 110 may be affixed to suture anchor 32. During certain suturing operations it is may be desirable to provide a suture anchor for use with surgical needle 100. Thus jaws 18 and 20 are provided with suture anchor recesses 28 and 30, respectively, which are configured to loosely hold a suture anchor, such as, for example suture anchor 32 (see FIG. 4d), between the jaws during initial insertion of surgical suturing apparatus 10 within the body of a patient. As best shown in FIG. 3, suture anchor recesses 28 and 30 are positioned offset from a center-line of jaws 18 and 20 to avoid interference with a portion of the needle securing mechanism, specifically a pair of blade channels, described in detail above.

Operation of The Securing Mechanism

Referring now to FIGS. 4a through 6b, the operation of passing surgical needle 100 repeatedly back and forth between jaws 18 and 20 will now be described. In FIG. 4a, needle 100 is secured in jaw 20 as reciprocating mechanism 74 is positioned such that arm 78 is in a distalmost position and arm 76 is proximalmost direction. In this positioning of arms 78, 76, side rods 72, 70 and thus blades 64, 62 assume advanced and retracted positions respectively. Thus, surgical needle 100 is retained within jaw 20 by engagement of blade 64 with notch 106 of surgical needle 100. In order to pass surgical needle 100 from jaw 20 to jaw 18, jaws 18 and 20 are closed by squeezing handles 33 and then control arms 76 and 78 are rotated in the direction of arrows A as indicated in FIGS. 5a. This clockwise rotation of arms 76, 78 advances side rod 70 and retracts side rod 72, thereby advancing blade 62 into engagement with notch 104 of surgical needle 100 and retracting blade 64 to disengage blade 64 from notch 106 as shown in FIGS. 5b and 5c respectively.

Referring now to FIGS. 6a and 6b, upon opening of jaws by way of handles 33, surgical needle 100 is locked within jaw 18 by the engagement of blade 62 with notch 104. To pass the needle 100 back to jaw 18, jaws 18 and 20 are closed and reciprocating mechanism 74, including arms 76 and 78, is rotated in a counter clockwise direction to cause blade 64 to advance to engage notch 106 of surgical needle 100 and simultaneously causing blade member 62 to retract and disengage from notch 104 surgical needle 100. This securing and releasing of the needle 100 from the respective jaw via movement of the blades 62, 64 by rotating wheel 80 can be repeated so that surgical needle 100 may be repeatedly passed back and forth between jaws 18 and 20 of surgical suturing apparatus 10.

The Lockout Mechanisms

As noted above, surgical suturing apparatus 10 is specifically designed to hold surgical needle 100 between jaws 18 and 20 when jaws 18 and 20 are in a closed position and secure or lock surgical needle 100 within one of jaws 18 and 20 whenever jaws 18 and 20 are in at least a partially opened condition to prevent surgical needle 100 from being inadvertently released from the jaws. This is accomplished by preventing reciprocating mechanism 74 from movement whenever jaws 18 and 20 are moved to at least a partially open position.

To prevent reciprocating mechanism 74 from moving, wheel 80 is provided with a pair of locking notches or slots 92 and 94 which correspond to the distalmost advancement of side rods 70 and 72, respectively. Slots 92 and 94 are configured to receive a lock pin 96 which is securely mounted to center rod 40. Thus as lock pin 96 advances within slot 92 or 94 of wheel 80, blades 62 and 64 are blocked or "locked out" from movement into or out of recesses 24 and 26, respectively. Thus, for example, as shown in FIG. 4a, when arm 78 is at a distalmost position, causing side rod 72 and thus blade 64 to engage notch 106 in surgical needle 100, upon opening of jaws 18 and 20, center rod 40 moves distally thereby carrying lock pin 96 distally, causing it to enter slot 94. Thus as jaws 18 and 20 are even partially opened, wheel 80 is blocked or "locked out" from rotation thereby securing blade 64 into engagement with surgical needle 100.

Referring to FIG. 5a, upon fully closing jaws 18 and 20, and center rod 40 is moved to a proximalmost position thereby drawing lock pin 96 out of engagement with the locking slot 94. Thus reciprocating mechanism 74, i.e., wheel 80, is free to rotate in either direction when center rod 40 is in a proximalmost position and jaws 18 and 20 are cammed closed. Upon rotation of arms 78 and 76 to cause the retraction of side rod 72 and the advancement of rod 70, slot 92 is brought into alignment with lock pin 96. As shown in FIGS. 5a through 5c, blade 64 is brought out of engagement with notch 106 of surgical needle 100 (FIG. 5b) and blade 62 is advanced into engagement with notch 104 of surgical needle 100 (FIG. 5c). Referring to FIG. 6a upon opening of jaws 18 and 20, pin 96 advances into slot 92 thereby again locking wheel 80 against any rotational movement. Thus upon opening jaws 18, 20, surgical needle 100 is firmly locked into jaw 18 by engagement of blade 62 with notch 104. This blade lockout mechanism insures that surgical needle 100 is firmly secured in either jaw 18 or 20 upon opening jaws 18, 20, thereby insuring surgical needle 100 is not released from the jaws during a suturing operation.

Referring to FIG. 5a, as arms 76 and 78 (and thus wheel 80) are rotated between a position aligning slot 92 with lock pin 96 and a position aligning slot 94 with lock pin 96, a side or abutment edge 98 of wheel 80 abuts lock pin 96 thereby holding center rod 40 in a proximalmost position. This arrangement provides a jaw lockout mechanism by preventing center rod 40 from moving until slot 92 or 94 becomes aligned with pin 96, thereby preventing jaws 18, 20 from opening while blades 64 or 62 are moved into their fully advanced and retracted positions for securely locking surgical needle 100 within one of jaws 18 or 20 respectively. Thus, surgical suturing apparatus 10 additionally has a jaw lockout mechanism which functions in conjunction with the blade lockout mechanism. Preferably the pin 96 is formed with a flat edge 97 as shown in FIG. 5d.

Figure 22:
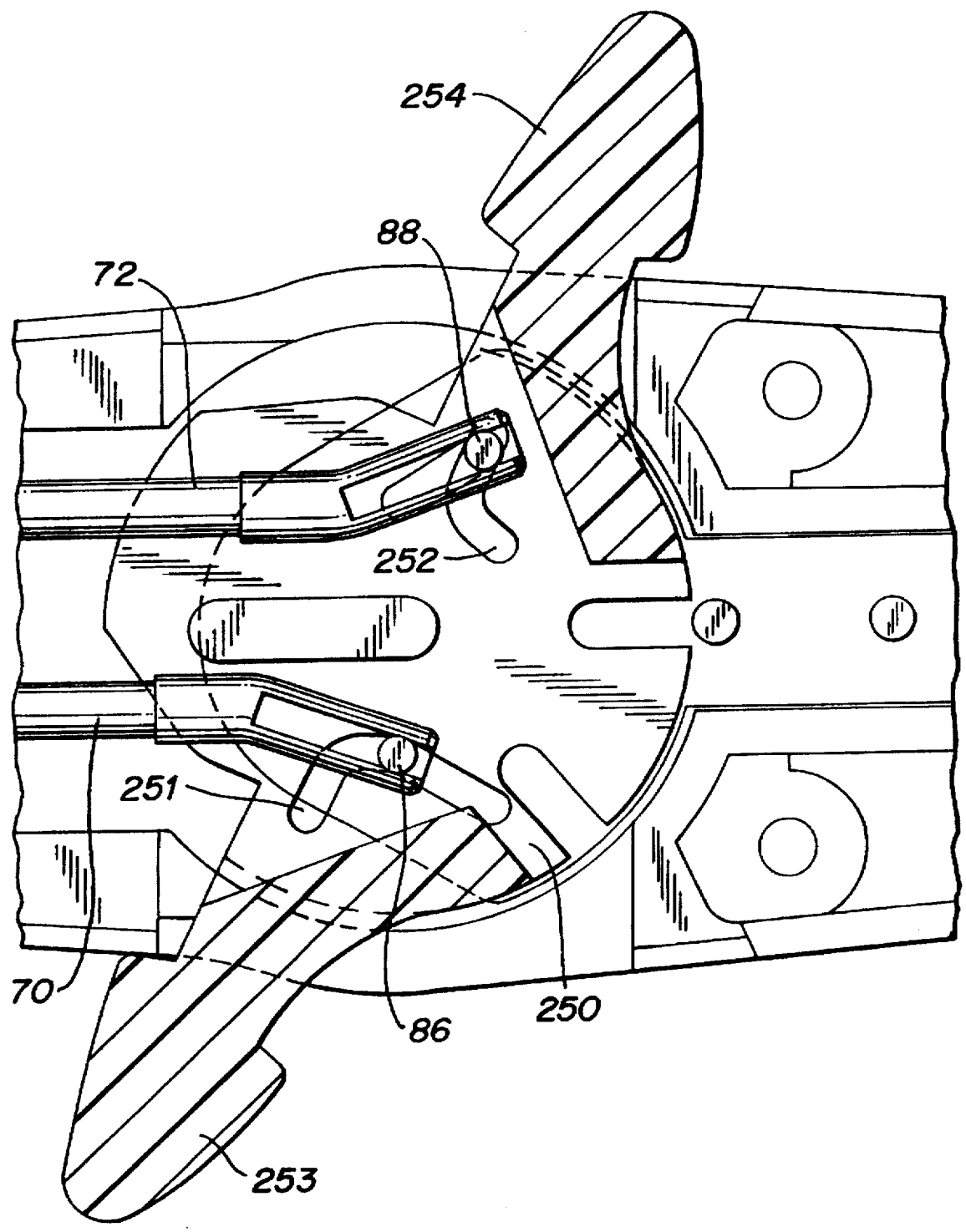
FIG. 22 is an plan view of an alternate embodiment of a wheel for use in the surgical instruments depicted in FIGS. 1 and 15A.

In addition, wheel 80 may alternately be configured as wheel 250 in FIG. 22. Cam slots 251 and 252 are angled in this embodiment, so that rods 70 and 72 may be pushed forward and backward as described above to alternately lock the surgical needle in jaws 18 and 20 using less longitudinal space in the jaws. In addition, the bend in slots 251 and 252 incorporate "cam timing" into the operation of the reciprocating mechanism, i.e., when pins 86 and 88 travel to the bend in slots 251 and 252, respectively, due to proximal movement of the corresponding side arm (253 and 254, respectively), the pins move distally, reach the bend and then move horizontally. If the corresponding side arm is moved distally, pin 86 or 88 travels horizontally, reaches the bend and then moves proximally, drawing its corresponding rod (70 or 72) with it. When pins 86 and 88 are either in the bend or moving horizontally, they "dwell", i.e., wheel 250 is moving, but the corresponding side rod (70 or 72, respectively) will not move. This feature reduces the amount of longitudinal space required in the jaws for the blades 62 and 64 to advance, allowing the jaws 18 and 20 to be made shorter because the dwell prevents further forward movement of the blade after it has engaged the needle. In other words, the dwell feature prevents the blade from moving beyond the distance required to engage it with the needle to secure the needle in one of the jaws.

The Lockout Override Mechanism and Loading Units

As noted hereinabove, surgical needle 100 is held between jaws 18 or 20 when they are in a closed position and secured into one of jaws 18 or 20 when jaws 18 and 20 are moved into an open position. Therefore, in order to load a surgical needle into jaws 18 or 20, there is provided an override mechanism which is configured to disengage the blade and jaw lockout mechanisms of surgical suturing apparatus 10.

Referring initially to FIGS. 2 and 2a it can be seen that wheel 80 is rotatably mounted on a U-channel 118 which is slidably disposed within housing halves 14a and 14b. Wheel 80 is rotatably mounted on U-channel 118 by means of a pair of plungers 120 which are transversely slidable through holes 122 in wheel 80 and holes 124 in U-channel 118. Plungers 120 are each provided with smaller diameter plunger knobs 126 which are capable of riding longitudinally within longitudinal channels 128 formed in housing halves 14a and b. Plungers 120 are both biased outwardly away from the center of surgical suturing apparatus 10 by a pair of spring washers 130. Plungers 120 may also be biased by coil springs shown as 130A in FIG. 2B rather than spring washers 130. As shown in FIG. 2b, when the override mechanism is in an inactivated condition, plunger 120 is biased upwardly or outwardly into engagement with a surface 132 of housing 14 by coil spring 130A or spring washer 130 (not shown in FIG. 2B).

To activate the override mechanism, jaws 18 and 20 are closed and arms 76 and 78 are placed in a centered position, i.e., perpendicular to handle housing 14. The override mechanism is activated by depressing small diameter knobs 126 inwardly against bias of spring washers 130 or coil springs 130A causing larger diameter portion of plungers 120 to be moved out of engagement with surface 132 of housing 14. As plunger 120 is disengaged from surface 132, a spring 134, positioned in recess 135 between U-channel 118 and housing member 14 and initially in a compressed state, is released thereby propelling the override mechanism, including wheel 80, distally into a recess 136 in housing 14 (FIG. 2B). As wheel 80 (including plunger 120) moves distally within recess 136, knobs 126 move distally within longitudinal channels 128 in housing 14. A hole 138 in U-channel 118 allows center rod 40 to extend through and move within U-channel 118 and through spring 134.

Referring now to FIGS. 7a through 8b, when wheel 80 is propelled forward as described above, side rods 70 and 72 and thus blades 62, 64 are driven distally. As shown in FIGS. 7b, 7c and 8b blades 62 and 64 are each provided with notched out or recessed areas 114 and 116, respectively. Thus, as blades 62, 64 are driven distally, notches 114 and 116 align with needle receiving recesses 24 and 26 in jaws 18 and 20, respectively. As shown in FIG. 7a, when jaws 18 or 20 are in a closed position, lock pin 96 is spaced from abutment edge 98 of wheel 80. Upon releasing handles 33, jaws 18 and 20 are allowed to pivot open as described above and center rod 40 and thus lock pin 96 are free to move distally to open jaws 18 and 20. In the absence of the override mechanisms this would not be the case as lock pin 96 would engage abutment edge 98 thereby preventing the jaws from opening. Thus it can be seen that the override mechanism of surgical suturing apparatus 10 enables blades 62 and 64 to be disassociated with surgical needle 100 while at the same time allowing jaws 18 and 20 to be moved to an open position for loading. Accordingly, upon activation of the override mechanism, surgical needle 100 may be inserted within recesses 24 and 26 without engagement with either of blades 62 or 64.

Upon positioning surgical needle 100 between jaws 18 and 20 and in alignment within recesses 24 and 26, arms 76 and 78 may be pulled proximally thereby causing wheel 80 and thus U-channel 118 to recompress spring 134. As wheel 80 is moved proximally plungers 120 reengage surfaces 132 and housing 14, thereby rearming the lockout mechanisms and deactivating the override mechanism.

It will be noted that in order to activate the override mechanism jaws 18 and 20 are placed in the closed position, arms 76 and 78 are in a centered position and both plungers 120 are depressed simultaneously. Thus, multiple, simultaneous steps must be performed to release the override mechanism thereby preventing inadvertent activation of the override mechanism and inadvertent release of surgical needle 100. Alternatively, the function of the override mechanism could also be accomplished by moving wheel 80 proximally, provided recesses similar to 114 and 116 described above would be located on blades 62 and 64 in such a way that the proximal movement of wheel 80 would align recesses 114 and 116 with needle receiving recesses 24 and 26 as described above.

Referring now to FIG. 9 there is disclosed a loading unit or mechanism 140 for replacing surgical needle 100 and associated length of suture material 110, and optionally a suture anchor 32, within surgical suturing apparatus 10. Loading mechanism 140 generally consists of a handle 142 and arms 144 and 146 attached thereto via fasteners 148. Each of arms 144 and 146 is adapted to hold either anchor 32 or surgical needle 100. Anchor 32 and surgical needle 100 are preferably of approximately the same diameter so that both arms 144 and 146 may be of similar dimensions. Preferably surgical needle 100 and suture anchor 32 are retained within slots 152 or 150 formed within arms 146 and 144, respectively.

Referring now to FIG. 10 there is disclosed an alternate embodiment of a loading unit or mechanism suitable for use with the surgical suturing apparatus 10. Loading mechanism 154 is designed to support surgical needle 100 within a notch 156 therein. Jaw receiving recesses 158 and 160 are positioned adjacent either side of surgical needle 100 and are configured to receive jaws 18 and 20 in an opened condition and align needle recesses 24 and 26 with ends 102 of surgical needle 100. Preferably, body portion 162 has a hollow cavity and is capable of holding an associated length of suture material and, optionally, a suture anchor within the cavity. Loading mechanism 154 may additionally be provided with alignment structure 164 which aids in aligning body portion 16 on the loading mechanism.

Additional loading units particularly suited for use with surgical suturing apparatus 10 are disclosed in U.S. Patent Applications entitled Mechanism For Endoscopic Suturing Device and Surgical Suturing Apparatus With Loading Mechanism filed Aug. 19, 1994, Ser. Nos. 08/293,234 and 08/293,233, respectively, the disclosures of which are incorporated by reference herein.

To load a surgical needle 100 along with the associated length of suture material 110 and, optionally, suture anchor 32, within surgical suturing apparatus 10, override mechanism is activated by depressing plungers 120 as described above, thereby allowing both blades 62 and 64 to move distally and aligning notches 114 and 116 with needle recesses 24 and 26, respectively, as described hereinabove (FIGS. 7a through 7c). Referring now to FIG. 11, jaws 18 and 20 are positioned about arms 144 and 146 and surgical needle 100 is initially positioned with one of the jaw recesses such as, for example, needle recess 24 in jaw 18. Optionally suture anchor 32 is positioned in alignment with suture anchor recesses 28 and 30 in jaws 18 and 20, respectively. At this point surgical needle 100 rests within recess 24 and is surrounded by notch 114 of blade 62. Because notch 114 aligns with recess 24 surgical needle 100 is freely insertable therein as shown in FIGS. 8a and 8b. As noted above, jaws 18 and 20 can now be closed in a manner described above thereby causing surgical needle 100 to enter needle recess 26 in jaw 20. Blade 64 is also in a distalmost position aligning notch 116 with a needle recess 26. In this manner jaws 18 and 20 are completely closed about surgical needle 100 without engaging blades 62 or 64 with surgical needle 100.

Upon drawing arms 78 and 76 proximally, wheel 80 and thus U-channel 118 move proximally compressing spring 134 and allowing plungers 20 reengage surfaces 132 of housing 14. In this manner the override mechanism is deactivated and blades 62 and 64 are drawn proximally into engagement with notches 104 and 106 of surgical needle 100. Referring to FIG. 5a, when jaws 18, 20 are in the closed position lock pin 96 is clear of slots 92, 94 in wheel 80 allowing wheel 80 to rotate freely to reciprocate blades 62 and 64. Lock pin 96 rides against abutment edge 98 thereby preventing jaws 18 and 20 from being opened until surgical needle 100 is engaged by one of blades 62 or 64. Thus, upon rotation of arms 76 and 78, one of the blades, such as, for example, blade 64 in FIG. 4a, is advanced to engage, for example, slot 106 of surgical needle 100. Again, and as noted above, as jaws 18, 20 are released to an open position, lock pin 96 will engage slot 94 thereby locking out blade 64 from having further movement. In this manner surgical needle 100 has been positively and firmly located within jaw 20 and is locked into jaw 20 when jaws 18 and 20 are moved to an open position. Apparatus 10 is now ready for use in a surgical suturing operation.

Operation Of The First Embodiment

Figure 23A:
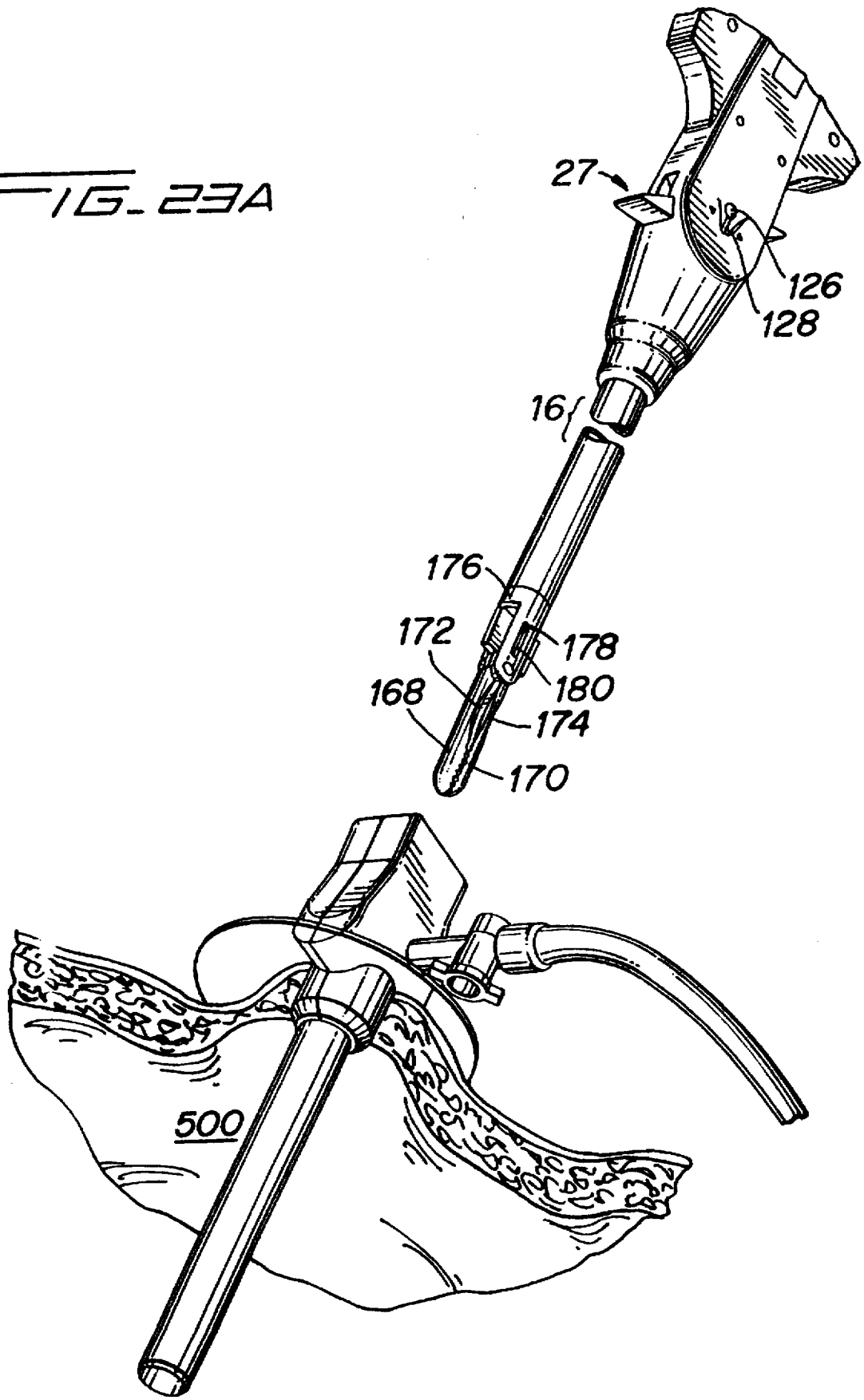
FIG. 23A is a perspective view of the instrument of FIGS. 1 and 15A about to be placed in a trocar, the trocar having already been inserted into a body cavity.

Referring now to FIGS. 12 through 14 along with FIGS. 4a through 6a, and initially referring to FIG. 12 and FIG. 4a, prior to use, surgical needle 100 is secured within a jaw, such as, for example, jaw 20 in the manner described hereinabove. When used during endoscopic or laparoscopic procedures, jaws 18 and 20 are moved to the closed position and inserted, along with a portion of body portion 16, through a cannula or trocar such as cannula 500 as depicted in FIGS. 23A, 23B and 23C, i.e., the instrument with its jaws closed is placed into a cannula as shown in FIGS. 23A and 23B. The jaws are then opened as shown in FIG. 23C. Preferably associated length of suture material 110 is affixed to surgical needle 100. As shown in FIGS. 12 and 23C, once inside the body cavity jaws 18 and 20 are moved to the open position and positioned about tissue sections A and B to be sutured.

Referring to FIG. 13, jaws 18 and 20 are moved to a closed position to cause surgical needle 100 to pierce tissue sections A and B. As shown in FIGS. 5a through 5c, upon rotation of arms 78 and 76 of wheel 80 in a clockwise direction, side rod 72, and thus blade 64 is retracted out of engagement with surgical needle 100, side rod 70 is advanced and thus blade 62 is simultaneously moved into engagement with notch 104 and surgical needle 100. The surgical needle 100 is held between closed jaws 18 and 20 of surgical suturing apparatus 10 while blades 62 and 64 are in motion. As shown in FIG. 5b, blade 64 is disassociated with surgical needle 100 and blade 62 is engaged with surgical needle 100 as shown in FIG. 5c. Upon releasing handles 33, spring 56 biases jaws 18 and 20 into the open position thereby drawing surgical needle 100 through tissue sections A and B as shown in FIG. 14. It will be noted that during the entire operation, surgical needle 100 is secured into jaw 18 or 20 when jaws 18, 20 are in the open position or is held between jaws 18 and 20 when jaws 18 and 20 are in a closed position while the surgical needle is being transferred, thus ensuring consistent control of surgical needle 100 during all phases of a surgical suturing operation.

As noted hereinabove, surgical needle 100 may be passed back from jaw 18 to jaw 20 by reversing the process and repiercing tissue sections A and B to form another stitch. In this manner, a line of endoscopic sutures or stitches can be created. To reinforce such a line of stitches, another line of stitches may be placed adjacent a first line. In addition, this instrument may be used to create a knot at the beginning or end of a line of stitches to secure that line. This instrument can be used, for example, in operations such as Nissen fundoplication or bladder-neck suspension.

Optionally, it will be noted that a surgical needle may be utilized having one pointed end which pierces tissues A and B and is then transferred to the opposing jaw 18. The needle could then be passed back to jaw 20 prior to penetration of tissue at which time the pointed end of surgical needle 12 could re-penetrate tissue and be transferred from jaw 20 to 18 again to form another stitch.

Alternate Embodiment

Referring now to FIGS. 15a through 18 there is disclosed an alternate embodiment of a surgical suturing apparatus. Apparatus 166 is substantially identical to apparatus 10 described hereinabove with a few notable modifications.

Referring initially to FIG. 15a, apparatus 166 has pair of jaws 168 and 170 each of which has a narrowed cross-sectional area or waist portion 172 and 174, respectively. In use, upon closing jaws 168 and 170 of surgical suturing apparatus 166 about tissue sections, such as, for example tissue sections A and B described hereinabove with respect to FIGS. 12 through 14, waist portions 172 and 174 of jaws 168 and 170, respectively, aid in preventing the tissue from "bunching" up or clogging the jaw structure. Jaws 168 and 170 are pivotally affixed to a modified support member 176 which in turn is affixed to a distal end of body portion 16. Jaws 168 and 170 are opened and closed by means of two armed handle 33 in substantially the same manner as is disclosed above with respect to surgical suturing apparatus 10. However, center rod 40 is provided with a guide pin 178 in place of pin 42. Pin 178 extends between a pair of guide slots 180 in support member 176 and serves to ensure against rotational deflection of center rod 40 during its reciprocal movements. Pin 178 riding within slot 180 allows maximum force to be transferred to the jaws to help facilitate closing of the jaws around the tissue to be sutured. Additionally, handle housing 14 may be provided with a defined surface area 182 which is particularly suited for use with labeling or other marking methods to identify the surgical suturing apparatus.

Referring now to FIGS. 15b and 15c, when jaws 170 and 168 are in an open position, center rod 40 is biased distally. Thus, guide pin 178 is in a distalmost position within slot 180. Surgical needle 100 is retained within jaw 168 by engagement with blade member 64 in a manner substantially identical to that described above. It will be noted that at this stage, lock pin 96 engages slot 94 to prevent any reciprocal movement of blade 64 and 62, thereby ensuring surgical needle is secured within jaw 168 when jaw 169 and 170 are in an open position. Still referring to FIG. 15b, surgical suturing apparatus 166 is preferably provided with a pair of guide rod and seals including front seal 184 and rear seal 186. Two identical seals 184 and 186 are provided to prevent the escape of insufflation gas out of the body cavity during surgery. Referring to FIG. 15d, each seal 184 and 186 has, at one end, a center rod hole 188 for receipt of center rod 40 therein and a pair of blade slots 190 and 192 for receipt of blades 64 and 62 respectively therein. The other end of each seal has a single opening 194 to accommodate center rod 40 and blades 64 and 62. Each seal is shaped to press fit engage the seal in front of it and to help maintain pressure in the body cavity, i.e., seal lip 196 engages the inside surface of seal 186 to prevent gas from leaking.

Referring now to FIG. 16, as handles 33 are partially closed, center rod 40 is drawn proximally thereby drawing pin 178 proximally to an intermediate position within slot 180.

Referring now to FIGS. 18a and 18b, as handles 33 are pivoted fully closed, guide pin 178 reaches its proximalmost position within slot 180 and jaws 168 and 170 are cammed fully closed. As noted hereinabove with respect to surgical suturing apparatus 10, once handle 33 has been pivoted fully closed, pin 96 affixed to center rod 40 is drawn to a proximalmost position clear of slot 94 in wheel 80. Thus wheel 80 is freed up for rotation to reciprocally move blade 62 and 64 within jaws 170 and 168, respectively. As noted above, as arms 78 and 76 are rotated clockwise slot 92 aligns with pin 96. Further, flat edge 97 on pin 96 prevents premature entry of pin 96 into the slots. Blade 62 is advanced within jaw 170 to engage surgical needle 100 and simultaneously and reciprocally blade 64 is retracted out of engagement with surgical needle 100. Upon releasing handles 33, lock pin 96 slides into slot 92 to thereby prevent the reciprocating mechanism 74 from any further rotational movement and thus locking surgical needle 100 within jaw 168 within jaw 170 as shown in FIG. 19.

Referring to FIG. 17, surgical suturing apparatus 166 may be provided with a blade guide assembly 198 which is designed to prevent flex in blades 62 and 64 during their reciprocal movement thereby maximizing the transfer of force to blades 62 and 64, helping to ensure their engagement with surgical needle 100. Guide assembly 198 generally includes a pair of guide tubes 200 and 202 which are configured for guidance and support of blades 64 and 62, respectively. Preferably guide tubes 200 and 202 are fixed to a rear stabilizing plate 204 mounted adjacent front seal 184. Plate 204 has a hole 205 for receipt of center rod 40. In this manner, guide assembly 198 helps ensure maximum force transmitted to blades 62 and 64 without loss due to flexion. Surgical suturing apparatus 166 is preferably provided with plunger knobs 126 which ride in housing channels 128 (FIG. 16) substantially similar to that described above with respect to plungers 120 of surgical suturing apparatus 10.

Alternate Jaw Structure

Referring now to FIGS. 20 and 21 there is disclosed another embodiment of a jaw structure suitable for use with either surgical suturing apparatus 10 or 166 described hereinabove. Jaw 206 includes pivot holes 208 for engagement with pivot pin 34 and a cam slot 210 for engagement with pin 42 and 178 mounted on center rod 40. Additionally, jaw 206 includes a longitudinal extending blade channel 212 which is substantially identical to channels 66 and 68 described hereinabove. Preferably a body portion 214 has a recessed underside edge 216 which allows a sufficient clearance area 217 for tissue to be contained between the jaws as shown in FIG. 21. Additionally, jaw 206 may be provided with an angled tip 218 which may have a flush or ridged surface as desired. A particular notable feature of jaw 206 is the provision of a tapered needle recess 220 which tapers from a diameter greater than that of a surgical needle inserted therein to a diameter at a recess outlet 222 substantially less than that of the surgical needle 100 disposed therein as shown in FIG. 21b. Alternatively, needle recess 220 may be blind at the outer edge of each jaw. This tapered or blind recess prevents surgical needle 100 from emerging from recess outlet 222 on the outside of the jaws. Any such egress would create a traumatic edge to the instrument and would therefore be undesirable. In addition, this arrangement centers needle 100 between the jaws, as neither end of the needle may project further from its jaw than does its counterpart.

Additionally, as further shown in FIG. 21b, needle recess 220 is more conventionally formed at an angle T of approximately five to ten degrees with respect to the vertical, and preferably on the order of an angle of six and a half degrees. This angle roughly coincides with the radius of curvature of the arcuate surgical needle 100 which, as noted herein above, is substantially equal to the distance between pivot pin 34 and the needle recess 220.

As shown in FIG. 24, the jaws may also be constructed with male and female members to help maintain a tissue gap between the jaws. Jaw 300 is the male member: it has projection 350 with projection 352 atop projection 350. Jaw 301 is the female member: it has projection 351 with recess 353 therein. When jaws 300 and 301 are fitted together, projections 350 and 351 meet, thereby preventing jaw tips 354 and 355 from ever fully meeting with each other. Projection 352, in turn, rides in corresponding recess 353 to facilitate the rotation of jaws 300 and 301 toward and away from each other. In addition, in manufacturing jaw 300, it is preferable to form projection 352 larger than required and subsequently crush that portion to accommodate the tight tolerance between the two jaws.

It will be understood that various modifications may be made to the embodiments disclosed herein. For example, the jaw structure and support member or elongate portion may be rotatably mounted with respect to the body portion. The jaw may articulate with respect to the elongated portion. Additionally, various other structures may be provided to block the reciprocating mechanism to ensure positive locking of a surgical needle within a jaw when the jaws are in an open condition, such as, for example, detents at each end of wheel rotation or other force requiring disengaging mechanisms. Other jaw lockouts may include a transverse lip formed on the wheel and engageable with the lock pin when the surgical needle is not held by only one jaw. Also, in place of the control arms, ridged edges of the wheel may project slightly beyond the handle housing thereby requiring deliberate action to operate the reciprocating mechanism. Various additional structure for axially moving the center rod may be provided such as for example, a screw or thread type mechanism to draw and drive center rod in the axially direction, as well as various flexible and non-flexible replacements for the center rods, side rods and elongate housing potion. Further, various handle configurations such as, for example, pistol grip type or single arm configurations may be substituted in place of the two arm handle disclosed hereinabove. Additionally, various surgical needles other than double-ended surgical needles may be used. Therefore, the above description should not be construed as limiting, but merely as exemplifications as preferred embodiments. Those skilled in the art will envision other modifications within the scope and spirit of the claims appended hereto.

What is claimed is:

1. An apparatus for manipulating a surgical needle comprising:
   a) a body portion;
   b) a first movable needle receiving jaw extending from a distal end of the body portion and having a first needle engaging member;
   c) a second movable needle receiving jaw extending from the distal end of the body portion and having a second needle engaging member, wherein each of the first and second needle receiving jaws has a recess for receipt of a portion of a surgical needle therein;
   d) a wheel rotatably mounted within the body portion, a proximal end portion of each of the first and second needle engaging members connected to opposing sides of the wheel such that rotation of the wheel simultaneously retracts one of the needle engaging members and advances the other; and
   e) a pair of tubes disposed within the body portion wherein said needle engaging members extend through said tubes.

2. The apparatus as recited in claim 1, wherein at least one of the first and second recesses is circular in cross-section.

3. The apparatus as recited in claim 2, wherein at least one of the first and second recesses tapers to a width less than that of a surgical needle inserted therein.

4. The apparatus as recited in claim 1, further comprising a force-transfer mechanism operatively associated with the first and second needle receiving jaws for preventing the jaws from twisting.

5. Surgical apparatus for manipulating a surgical incision member comprising:
   a) an elongated body portion having a proximal and distal portion;
   b) first and second jaw elements extending from the distal portion of said body portion, at least one of said jaw elements being movable between an open and closed position;
   c) a surgical incision member supported by one of said jaw elements;
   d) a handle extending from the proximal portion of said body portion for moving said jaw elements between said open and closed positions; and
   e) at least one seal positioned between the handle and the jaw elements to prevent the egress of gas from the body cavity;
   wherein said at least one jaw element is prevented from moving when said surgical incision member is not secured in at least one of said jaw elements.

6. The apparatus as recited in claim 5, wherein the seal comprises two individual elements in sequence and is positioned within the elongated body portion.

7. The apparatus as recited in claim 6, further comprising at least one needle enagaging member movable with respect to said first and second jaw elements to selectively engage and disengage the surgical incision member.

8. The apparatus as recited in claim 7, further comprising a rotatable control handle to selectively move the at least one needle engaging member.

9. A method of manipulating a surgical needle inside a body cavity comprising the steps of:

a) inserting a cannula into a body cavity;

b) providing a surgical instrument having a control mechanism, a first jaw and a second jaw, at least one of the jaws being mounted for movement between a first position adjacent the other jaw and a second position spaced apart from the other jaw;

c) inserting said jaws through the cannula into the body cavity;

d) opening the jaws inside the body cavity to expose a pointed tip of the surgical needle secured in the first jaw;

e) passing the surgical needle through the tissue to be sutured; and f) selectively and mechanically manipulating the control mechanism to move a first needle engaging portion to a disengaged position to release the needle from the first jaw and to move a second needle engaging portion to an engaged position to secure the needle in the second jaw to allow transfer of control of the needle from the first jaw to the second jaw.

10. The method as recited in claim 9, further including the step of closing the jaws prior to transferring the needle from the first jaw to the second jaw.

11. The method as recited in claim 9, further including the step of rotating the control mechanism to slide the needle engaging portions with respect to the first and second jaws.

12. The method as recited in claim 9, further including the step of closing the jaws prior to insertion through the cannula.

13. A method of manipulating a surgical needle inside a body cavity comprising the steps of:

a) inserting a cannula into a body cavity;

b) providing a surgical instrument having first and second jaws, a handle mechanism for moving at least one of the jaws between a first position adjacent the other jaw and a second position spaced apart from the other jaw, and a control mechanism for releasing the needle from one jaw and securing the needle in the other jaw;

c) inserting said jaws through the cannula into the body cavity;

d) manipulating the handle mechanism with one hand to open the jaws inside the body cavity;

e) manipulating the handle mechanism with the same hand to close the jaws; and f) manipulating the control mechanism with the same hand to release the needle from one jaw and secure the needle in the opposing jaw.

14. The method as recited in claim 13, wherein the step of manipulating the control mechanism with the same hand to release the needle from one jaw and secure the needle in the opposing jaw includes rotating the control mechanism.

15. The method as recited in claim 13, wherein the step of manipulating the handle mechanism with the same hand to close the jaws includes squeezing two portions of the handle mechanism toward each other.

16. The method as recited in claim 14, wherein the step of rotating the control mechanism moves a first needle engaging portion to a position disengaged from said first jaw to release the needle from the first jaw and moves a second needle engaging portion to a position engaged with said second jaw to secure the needle in the second jaw.

17. The method as recited in claim 15, wherein the step of squeezing the two portions of the handle mechanism toward each other drives a rod operatively connected to said first and second jaws proximally.

18. The method as recited in claim 13, wherein said first and second jaws are prevented from opening during the step of manipulating the control mechanism with the same hand to release the needle from one jaw and secure the needle in the opposing jaw until the needle is secured in the opposing jaw.

* * * * *